US010582925B2

(12) United States Patent
Marks et al.

(10) Patent No.: US 10,582,925 B2
(45) Date of Patent: Mar. 10, 2020

(54) DEVICES, SYSTEMS, AND METHODS FOR KNOTLESS SUTURE ANCHORS

(71) Applicant: Medos International Sarl, Le Locle (CH)

(72) Inventors: Jacob A. Marks, Mansfield, MA (US); Ami Shyam Joshi, Irving, TX (US)

(73) Assignee: MEDOS INTERNATIONAL SARL, Le Locle (CH)

( * ) Notice: Subject to any disclaimer, the term of this patent is extended or adjusted under 35 U.S.C. 154(b) by 479 days.

(21) Appl. No.: 15/425,332

(22) Filed: Feb. 6, 2017

(65) Prior Publication Data

US 2018/0221013 A1    Aug. 9, 2018

(51) Int. Cl.
| A61B 17/04 | (2006.01) |
| A61B 17/17 | (2006.01) |
| A61B 17/00 | (2006.01) |
| A61B 90/00 | (2016.01) |

(52) U.S. Cl.
CPC ...... *A61B 17/0482* (2013.01); *A61B 17/0401* (2013.01); *A61B 17/1796* (2013.01); *A61B 17/0483* (2013.01); *A61B 2017/00367* (2013.01); *A61B 2017/00407* (2013.01); *A61B 2017/00477* (2013.01); *A61B 2017/0409* (2013.01); *A61B 2017/0412* (2013.01); *A61B 2017/0458* (2013.01); *A61B 2090/0811* (2016.02); *A61B 2217/007* (2013.01)

(58) Field of Classification Search
CPC ............ A61B 17/0401; A61B 17/0482; A61B 17/0483; A61B 17/1796; A61B 2017/00367; A61B 2017/00407; A61B 2017/00477; A61B 2017/0409; A61B 2017/0412; A61B 2017/0458; A61B 2090/0811; A61B 2217/007

See application file for complete search history.

(56) References Cited

U.S. PATENT DOCUMENTS

| 4,832,551 A | 5/1989 | Wollar |
| 4,900,210 A | 2/1990 | Buchanan et al. |
| 5,380,288 A | 1/1995 | Hart et al. |
| 5,542,799 A | 8/1996 | Culpen |
| 5,741,102 A | 4/1998 | Everett et al. |
| 5,842,822 A | 12/1998 | Everett et al. |
| 5,851,219 A * | 12/1998 | Goble ............... A61B 17/0401 606/232 |

(Continued)

FOREIGN PATENT DOCUMENTS

| EP | 3085336 A1 | 10/2016 |
| WO | WO-2004112841 A2 | 12/2004 |

(Continued)

OTHER PUBLICATIONS

Extended European Search Report for EP App. No. 18155355.3 dated Sep. 27, 2018 (17 pages).

*Primary Examiner* — Jocelin C Tanner

(57) ABSTRACT

Various devices, systems, and methods for knotless suture anchors are provided. In general, a guide device can be cannulated and can be configured to slidably receive therein an inserter tool configured to deliver a suture anchor into a hole formed in bone, such as with a drill advanced through the guide device. The guide device with the inserter tool therein can be configured to be held as a unit by one hand of a person, e.g., a surgeon or other medical personnel.

23 Claims, 27 Drawing Sheets

(56) References Cited

U.S. PATENT DOCUMENTS

| | | | |
|---|---|---|---|
| 6,162,234 A | 12/2000 | Freedland et al. | |
| 7,232,455 B2 | 6/2007 | Pedlick et al. | |
| 8,574,238 B2 | 11/2013 | Zannis et al. | |
| 9,161,747 B2 | 10/2015 | Whittaker et al. | |
| 2005/0267478 A1* | 12/2005 | Corradi | A61B 17/064 606/916 |
| 2008/0216292 A1 | 9/2008 | Rudduck et al. | |
| 2010/0198156 A1 | 8/2010 | Rosch | |
| 2013/0158596 A1* | 6/2013 | Miller | A61B 17/0401 606/232 |
| 2014/0200587 A1 | 7/2014 | Pompee et al. | |
| 2014/0277128 A1 | 9/2014 | Moore et al. | |
| 2014/0358230 A1* | 12/2014 | Niese | A61B 17/04 623/13.14 |
| 2015/0012015 A1* | 1/2015 | Berelsman | A61B 17/0401 606/144 |
| 2016/0113757 A1* | 4/2016 | Diduch | A61B 17/8872 606/104 |
| 2016/0310125 A1 | 10/2016 | Spivey et al. | |

FOREIGN PATENT DOCUMENTS

| | | |
|---|---|---|
| WO | WO-2009023034 A1 | 2/2009 |
| WO | WO-2012096706 A1 | 7/2012 |

\* cited by examiner

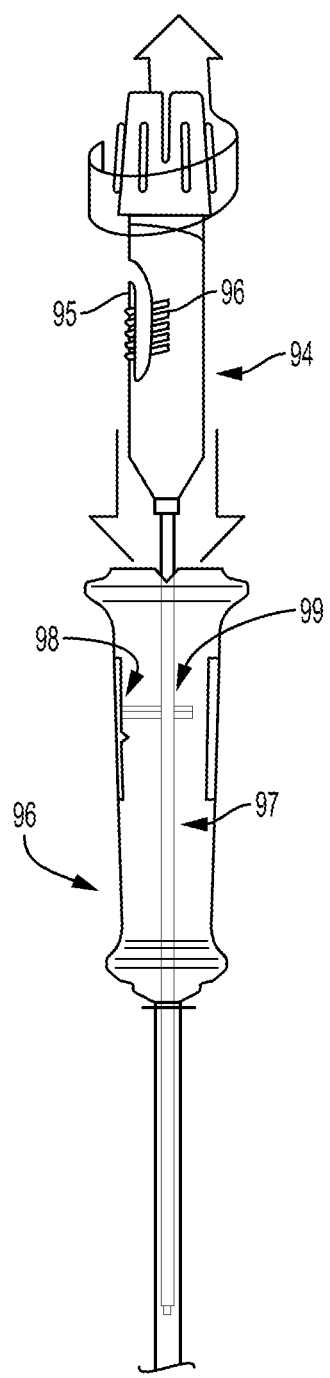
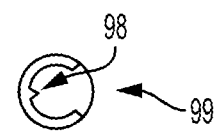
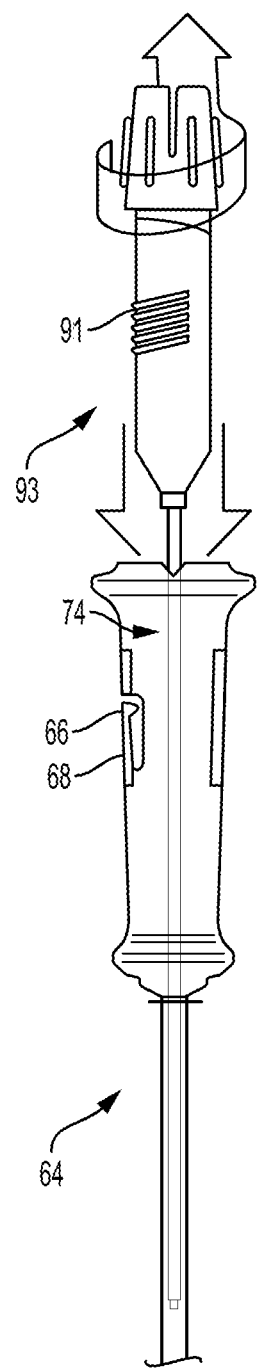
FIG. 11
FIG. 11A
FIG. 12

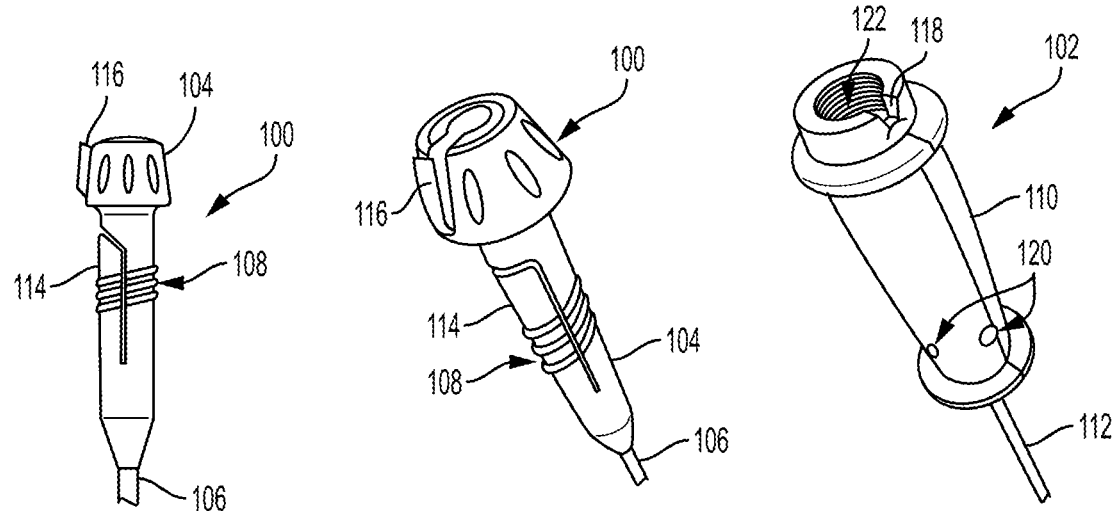
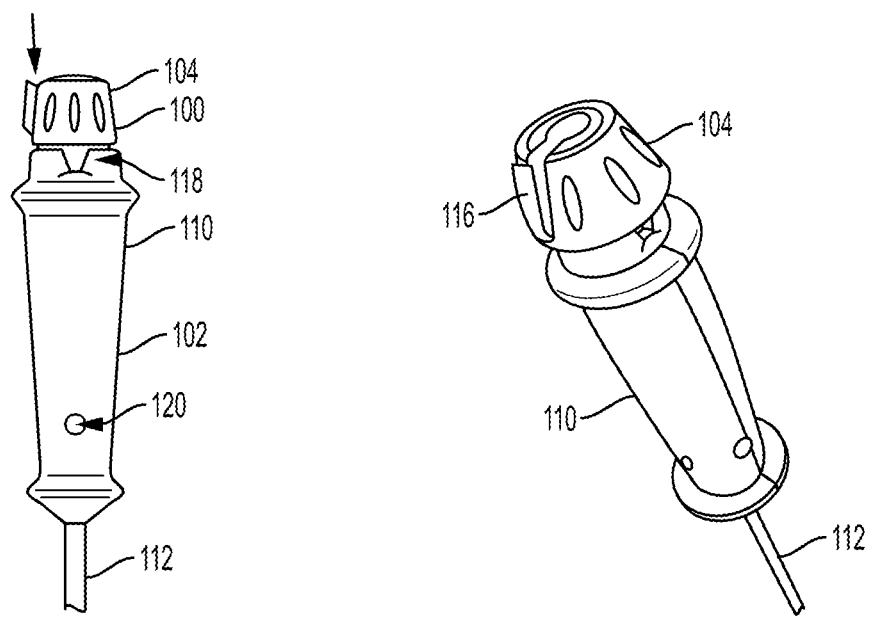

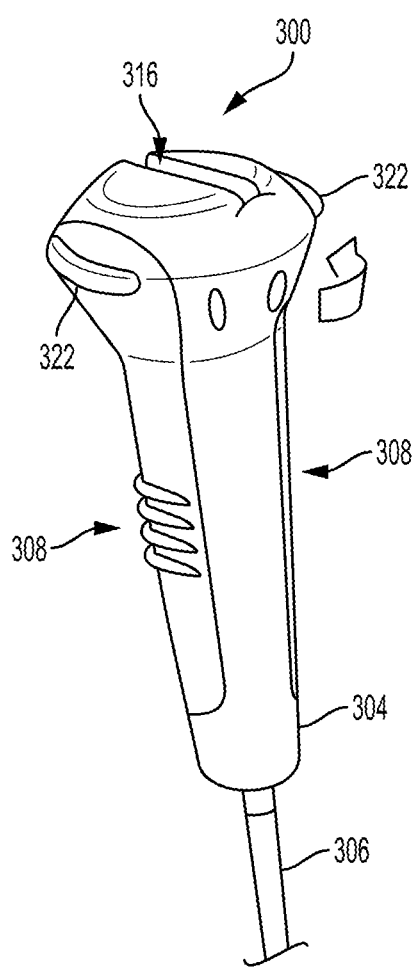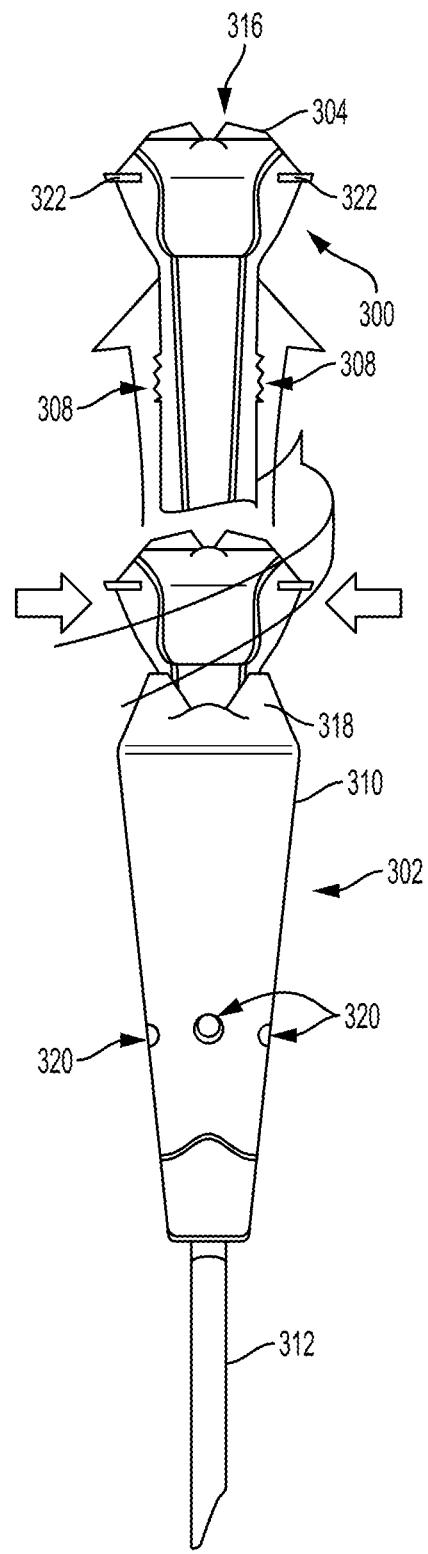
FIG. 27
FIG. 28

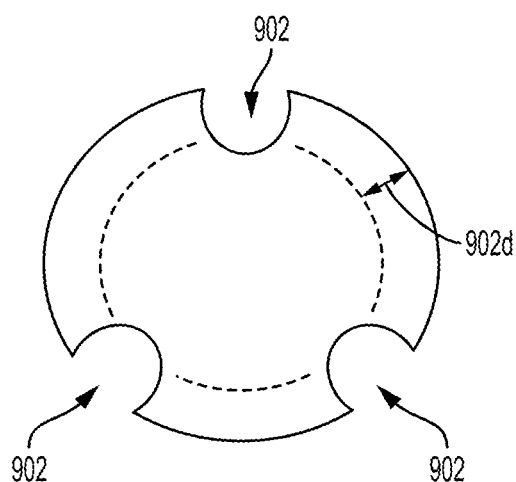
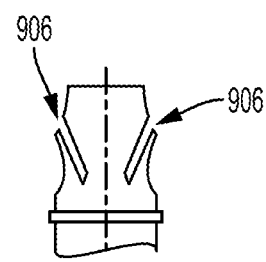
FIG. 46   FIG. 47
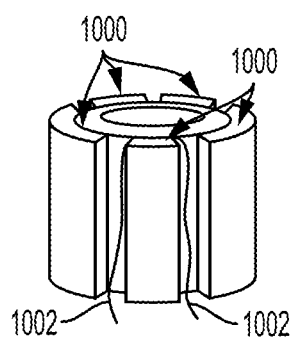 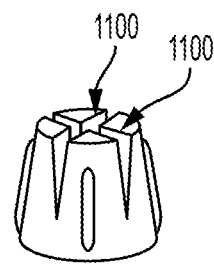 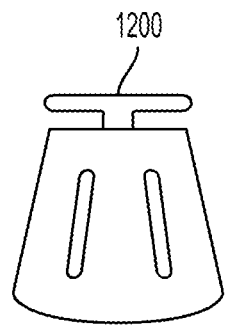
FIG. 48   FIG. 49   FIG. 50
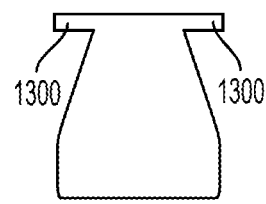
FIG. 51

DEVICES, SYSTEMS, AND METHODS FOR KNOTLESS SUTURE ANCHORS

FIELD

The present disclosure relates generally to devices, systems, and methods for knotless suture anchors.

BACKGROUND

When soft tissue tears away from bone, reattachment becomes necessary. Various traditional devices, including sutures, screws, staples, wedges, anchors, and plugs, have been used to secure soft tissue to bone. In ball-and-socket joints, such as the shoulder or hip, reattachment is often necessary due to the high stress and movement demanded of the ball-and-socket bone structures. Often, such procedures involve surgical reattachment of labral tissue. The labral tissue, or labrum, is a type of soft tissue or cartilage that surrounds the socket of ball-and-socket joints, such as the shoulder and the hip joint. The labrum forms a ring around the edge of the bony socket of the joint, and helps to provide stability to the joint, yet unlike bone, it also allows flexibility and motion.

Current surgical procedures can involve the use of a knotless suture anchor for reattaching the labrum to the bone, as knotless suture anchors avoid the need to tie a knot in a constricted space, such as a ball-and-socket joint. A suture is first passed through the tissue to be reattached, and the trailing ends of the suture extending outside of the patient are then loaded onto the anchor. A drill guide is typically passed through the tissue and positioned in alignment with the anchor site, and a drill bit is passed through the drill guide to form a hole in the bone. The suture is positioned off to the side while the hole is being formed. Once the bone hole is prepared, the drill guide is removed and the anchor can be inserted into the bone hole using an inserter tool. The suture is tensioned during advancement of the anchor so as to pull the tissue toward the bone hole, thereby anchoring the tissue to the bone.

While knotless suture anchors can be very effective in reattaching soft tissue to bone, the small size of the anchor and the tight constraints of the ball-and-socket joint can make it difficult to locate the bone hole and to insert the anchor into the bone hole. In the shoulder joint, for example, the humeral head will typically return to its resting position within the socket after the drill guide is removed, obstructing the path to the hole. In the hip, for another example, visualization of the hole can be a challenge due to challenging angles and the tight nature of the joint space.

Accordingly, there remains a need for improved devices, systems, and methods for knotless suture anchors.

SUMMARY

In general, devices, systems, and methods for knotless suture anchors are provided.

In one aspect, a surgical system is provided that in one embodiment includes a guide device having a handle and a first elongate shaft extending distally from the handle. The guide device has an inner lumen extending therethrough, has a first engagement feature on an inner wall of the guide device that defines the inner lumen, and is configured to guide a drill to a surgical site through the inner lumen thereof. The surgical system also includes an inserter tool having a second elongate shaft configured to be advanced distally through the inner lumen of the guide device with an anchor releasably coupled to a distal end of the second elongate shaft. The second elongate shaft has a second engagement feature on an outer surface thereof that is configured to engage the first engagement feature during the distal advancement of the second elongate shaft through the inner lumen of the guide device. Disengagement of the first and second engagement features is configured to automatically cause the anchor to be released from the distal end of the second elongate shaft.

The surgical system can vary in any number of ways. For example, the second elongate shaft can be configured to be advanced distally into the inner lumen of the guide device in a first type of motion relative to the guide device, and the second elongate shaft can be configured to be removed from the inner lumen of the guide device in a second, different type of motion relative to the guide device. The first and second engagement features can be configured to cooperate when engaged with one another to prevent the second elongate shaft from being removed from the inner lumen of the guide device using the first type of motion. The first type of motion can be longitudinal translation of the second elongate shaft through the inner lumen, and the second type of motion can be rotation of the second elongate about a longitudinal axis of the second elongate shaft. In at least some embodiments, the first and second engagement features can be configured to cooperate when engaged with one another to prevent the second elongate shaft from being removed from the inner lumen of the guide device by being longitudinally translated through the inner lumen in a proximal direction.

For another example, one of the first and second engagement features can be a thread, and the other of the first and second engagement features can be a tooth configured to threadably engage the thread. In at least some embodiments, the surgical system can also include an anchor, with a longitudinal length of the tooth not being less than a longitudinal length of the anchor.

For yet another example, the first elongate shaft can have a window formed in a sidewall thereof in a distal portion of the first elongate shaft, and the window can be configured to allow visualization therethrough of the anchor coupled to the distal end of the second elongate shaft.

For still another example, the inserter tool can have a handle with the second elongate shaft extending distally therefrom, and the handle of the inserter tool can be configured to abut the handle of the guide device when inserted therein to thereby prevent further distal advancement of the second elongate shaft through the inner lumen of the guide device. In at least some embodiments, the first and second engagement features can be configured to be engaged when the handle of the inserter tool is abutting the handle of the guide device.

For another example, the surgical system can include a suture configured to extend through the inner lumen of the guide device, and the inserter tool can be configured to be advanced distally through the inner lumen of the guide device over the suture with the suture coupled to the anchor.

For still another example, the surgical system can include at least one additional inserter tool having an elongate shaft and being configured to be advanced distally through the inner lumen of the guide device with an anchor releasably coupled to a distal end of the elongate shaft, each of the inserter tools being configured to releasably couple to a differently sized anchor.

In another embodiment, a surgical system is provided that includes a guide device having a first handle and a first elongate shaft extending distally from the first handle. The guide device has an inner lumen extending therethrough, and the guide device is configured to guide a drill through the inner lumen to allow the drill to drill a hole in bone. The surgical system also includes an inserter tool having a second handle and a second elongate shaft extending distally from the second handle. The second elongate shaft is configured to be advanced distally through the inner lumen of the guide device, with an anchor releasably coupled to a distal end of the second elongate shaft, by being one of longitudinally translated through the inner lumen and rotated about a longitudinal axis of the second elongate shaft relative to the guide device. The second elongate shaft is configured to be removed from the inner lumen of the guide device when the first and second handle are abutting one another only by being the other of longitudinally translated therethrough and rotated about the longitudinal axis of the second elongate shaft relative to the guide device.

The surgical system can have any of a number of variations. For example, the guide device can be configured such that removal of the second elongate shaft of the inserter tool from the inner lumen of the guide device automatically releases the anchor from the distal end of the second elongate shaft.

For another example, the first elongate shaft can have a first engagement feature on an inner surface thereof, and the inserter tool can have a second engagement feature on an outer surface thereof that is configured to automatically engage the first engagement feature during the distal advancement of the of the second elongate shaft through the inner lumen of the guide device and that is configured to automatically disengage from the second engagement feature in response to the removal of the second elongate shaft from the inner lumen of the guide device. One of the first and second engagement features can be a thread, and the other of the first and second engagement features can be a tooth configured to threadably engage the thread. In at least some embodiments, the first engagement feature can be a thread and the second engagement feature can be a tooth such that the second elongate shaft is configured to be advanced distally through the inner lumen of the guide device by being longitudinally translated therethrough, and the second elongate shaft is configured to be removed from the inner lumen of the guide device when the first and second handle are abutting one another only by being rotated about the longitudinal axis of the second elongate shaft relative to the guide device.

For still another example, the first and second handles can be configured to abut one another and thereby prevent further distal advancement of the second elongate shaft through the inner lumen of the guide device and position the anchor at a predetermined position relative to the guide device.

In another aspect, a surgical method is provided that in one embodiment includes passing a suture through tissue to be anchored to bone, passing a trailing end of the suture extending from the tissue through an inner lumen in a first elongate shaft of a guide device, advancing a drill through the inner lumen of the guide device to form a hole in the bone, advancing a second elongate shaft of an inserter tool over the suture in the inner lumen and through the inner lumen of the guide device to position an anchor, which is coupled to the suture and is releasably coupled to a distal end of the second elongate shaft, in the hole, and removing the second elongate shaft from the inner lumen of the guide device, thereby automatically releasing the anchor from the distal end of the second elongate shaft such that the anchor remains in the hole with the suture coupled to and extending from the anchor.

The surgical method can vary in any number of ways. For example, the first elongate shaft can have a first engagement feature on an inner surface thereof, and the second elongate shaft can have a second engagement feature on an outer surface thereof that automatically engages the first engagement feature during the advancement of the of the second elongate shaft through the inner lumen of the guide device and that automatically disengages from the second engagement feature in response to the removal of the second elongate shaft from the inner lumen of the guide device. In at least some embodiments, the second elongate shaft can be advanced through the inner lumen of the guide device by being longitudinally translated therethrough in a distal direction, the second elongate shaft can be removed from the inner lumen of the guide device by being rotated about a longitudinal axis of the second elongate shaft relative to the guide device, and the engagement of the first and second engagement features can prevent the second elongate shaft from being removed from the inner lumen of the guide device by being longitudinally translated therethrough in a proximal direction. In at least some embodiments, the second elongate shaft can be advanced through the inner lumen of the guide device until a handle of the guide device abuts a handle of the inserter tool, the abutment of the handles can indicate that the anchor is positioned within the hole, and the first and second engagement features can be engaged when the handle of the guide device abuts the handle of the inserter tool.

BRIEF DESCRIPTION OF DRAWINGS

This invention will be more fully understood from the following detailed description taken in conjunction with the accompanying drawings, in which:

FIG. 11 is a side, partially transparent view of still another embodiment of an inserter tool partially advanced into still another embodiment of a guide device;

FIG. 11A is a cross-sectional view of the guide device of FIG. 11;

FIG. 12 is a side, partially transparent view of another embodiment of an inserter tool partially advanced into the guide device of FIG. 9;

FIG. 17 is a side view of a proximal portion of another embodiment of an inserter tool;

FIG. 18 is a perspective view of the proximal portion of the inserter tool of FIG. 17;

FIG. 19 is a perspective view of a proximal portion of another embodiment of a guide device;

FIG. 20 is a side view of the inserter tool of FIG. 17 inserted into the guide device of FIG. 19;

FIG. 21 is a perspective view of the inserter tool of FIG. 18 inserted into the guide device of FIG. 19;

FIG. 27 is a perspective view of a proximal portion of yet another embodiment of an inserter tool;

FIG. 28 is a side view of the inserter tool of FIG. 27 being removed from yet another embodiment of a guide device;

FIG. 46 is a cross-sectional view of the inserter tool of FIG. 45;

FIG. 47 is a side view of a proximal portion of the inserter tool of FIG. 45;

FIG. 48 is a perspective view of a proximal portion of yet another embodiment of an inserter tool;

FIG. 49 is a perspective view of a proximal portion of still another embodiment of an inserter tool;

FIG. 50 is a side view of a proximal portion of another embodiment of an inserter tool;

FIG. 51 is a side view of a proximal portion of still another embodiment of an inserter tool;

DETAILED DESCRIPTION

Figure 1:
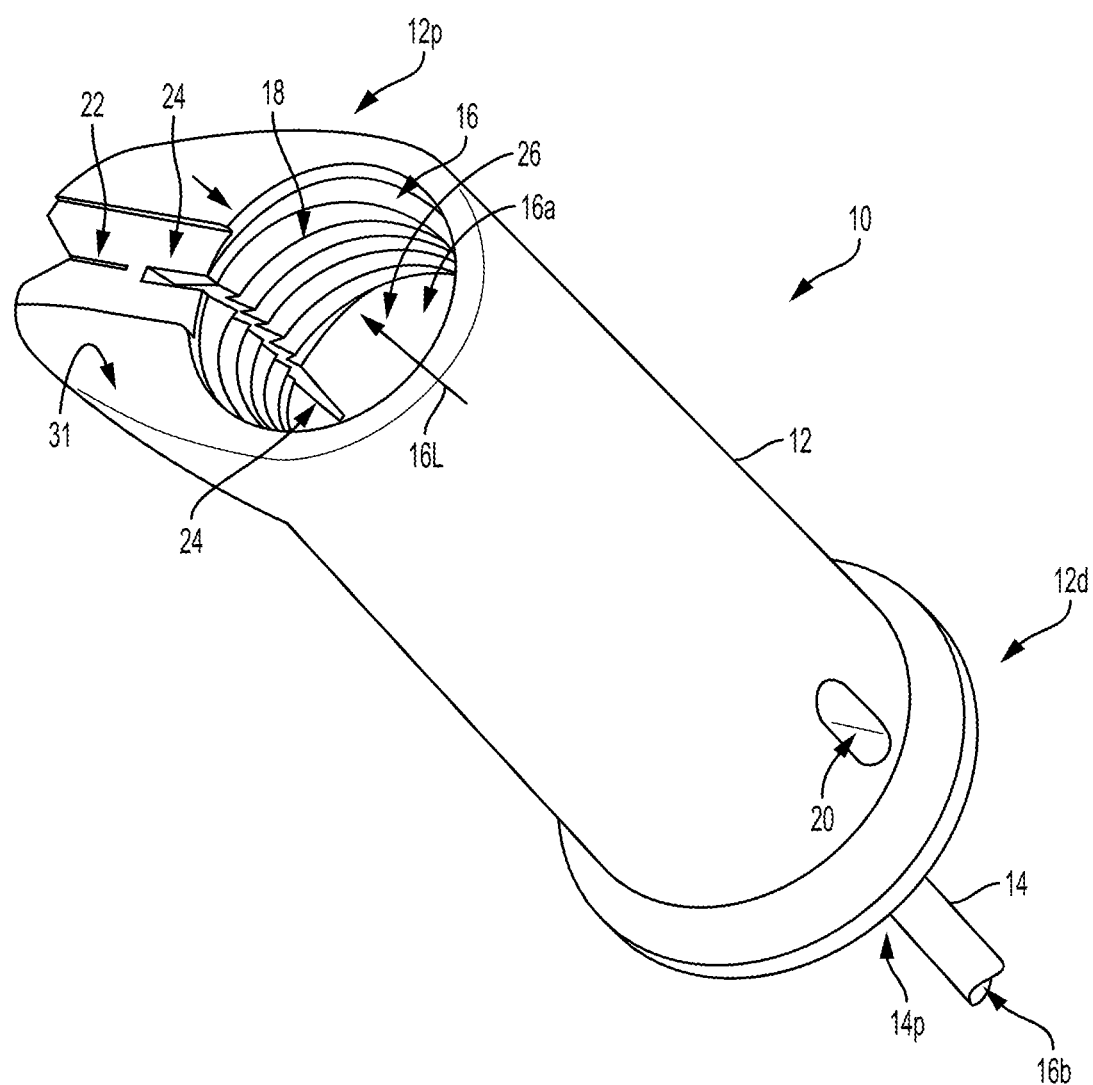
FIG. 1 is a perspective view of a proximal portion of one embodiment of a guide device.

Certain exemplary embodiments will now be described to provide an overall understanding of the principles of the structure, function, manufacture, and use of the devices, systems, and methods disclosed herein. One or more examples of these embodiments are illustrated in the accompanying drawings. Those skilled in the art will understand that the devices, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. A person skilled in the art will appreciate that a dimension may not be a precise value but nevertheless be considered to be at about that value due to any number of factors such as manufacturing tolerances and sensitivity of measurement equipment. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Devices, systems, and methods for knotless suture anchors are provided. In general, the devices, systems, and methods described herein can facilitate efficient delivery and deployment of a suture anchor in bone. A guide device can be cannulated and can be configured to slidably receive therein an inserter tool configured to deliver the anchor into a hole formed in the bone, such as with a drill advanced through the guide device. The guide device with the inserter tool therein can be configured to be held as a unit by one hand of a person, e.g., a surgeon or other medical personnel. The person's other hand may thus be free to perform other surgical tasks, such as holding another surgical instrument, e.g., a scope or other viewing device, a mallet, etc. The guide device with the inserter tool therein can be configured to be held by the single hand with the inserter tool being secured in a fixed position relative to the guide device, which may facilitate desired positioning of the anchor in the bone and/or may allow suture coupled to the anchor to be tensioned prior to release of the anchor from the inserter tool and thereby help ensure that tissue coupled to the suture is desirably positioned when the anchor is deployed.

The inserter tool can be configured to be removed from the guide device by only one type of motion, e.g., rotational motion about a longitudinal axis of the inserter tool or translational motion along the inserter tool's longitudinal axis. In this way, the inserter tool may be prevented from being prematurely withdrawn from the guide device and/or may be more intuitive for a person to use since the inserter tool can only be removed from the guide device in one way. The inserter tool can be configured to automatically release the anchor coupled thereto in response to being removed from the guide device, which may facilitate intuitive use of the inserter tool, may save time by allowing inserter tool removal and anchor deployment to occur simultaneously, and/or may help ensure that the anchor is not deployed until an intended time. The inserter tool can be configured to be inserted into the guide device using the other type of motion, e.g., the other of rotational motion and translational motion, which may further facilitate intuitive use of the inserter tool.

Figure 2:
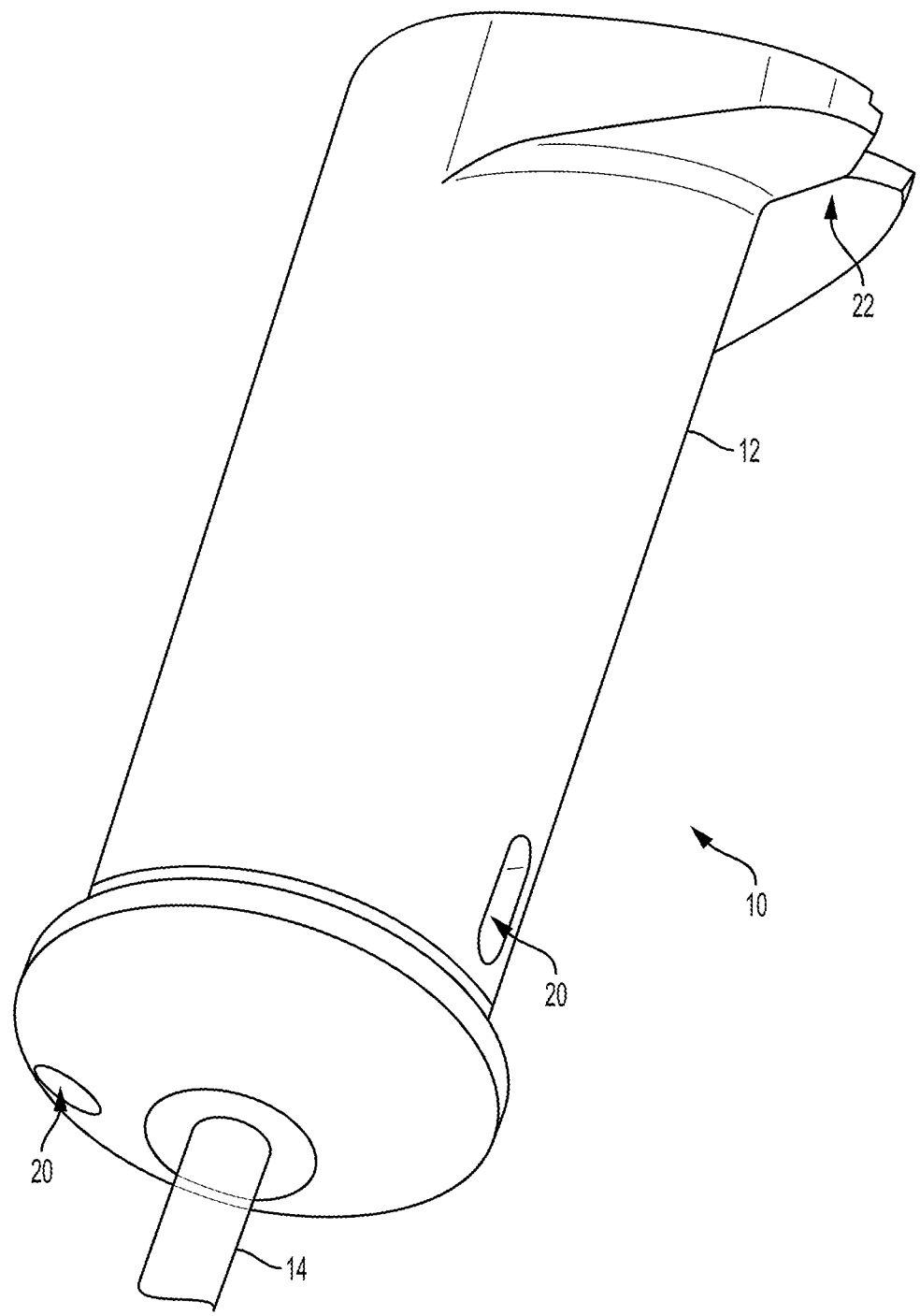
FIG. 2 is another perspective view of the proximal portion of the guide device of FIG. 1.
Figure 3:
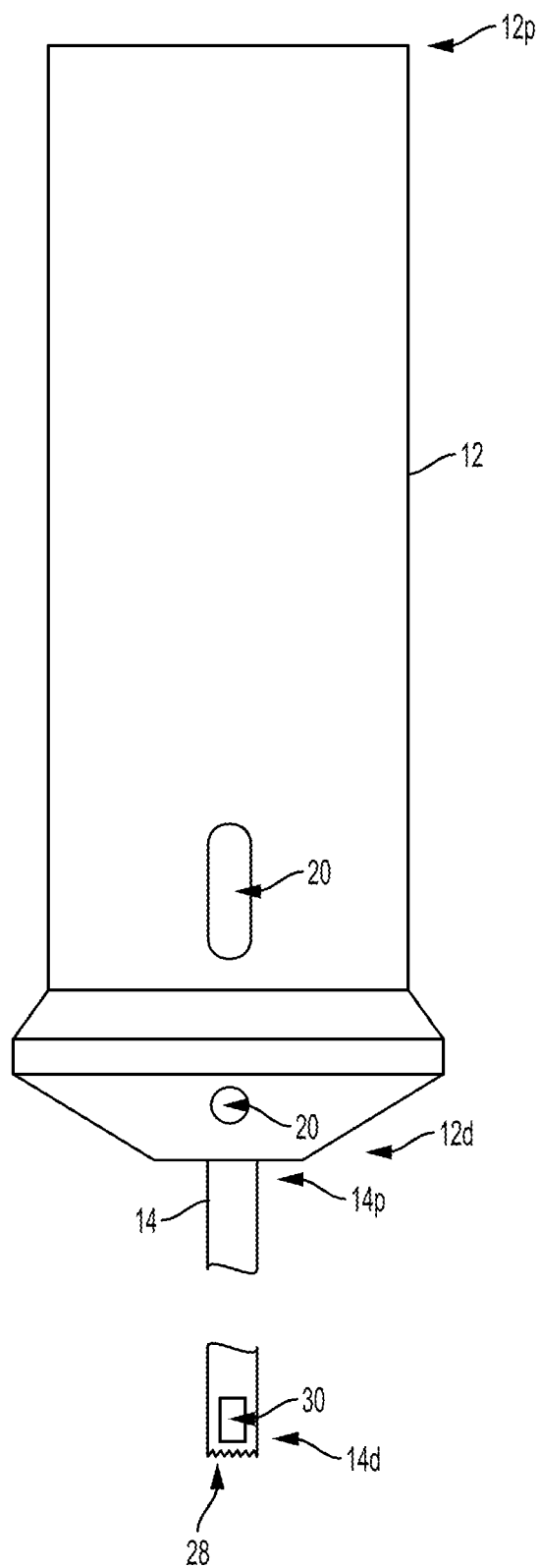
FIG. 3 is a side view of the proximal portion and a distal portion of the guide device of FIG. 1.

FIGS. 1-3 illustrate one embodiment of a guide device 10. The guide device 10 has a handle 12 and an elongate shaft 14 extending distally from the handle 12. The guide device 10 has an inner lumen 16 extending therethrough that is defined by an inner lumen 16a extending through the handle 12 and an inner lumen 16b coaxial with the handle's inner lumen 16a and extending through the shaft 14. The shaft 14 and the handle 12 are longitudinally aligned, but in other embodiments the handle 12 can extend at an angle from the shaft 14. Exemplary embodiments of guide device handles are further described in U.S. Pat. Pub. No. 2016/0310125 entitled "Knotless Suture Anchor Guide" filed Apr. 23, 2015, which is hereby incorporated by reference in its entirety.

The handle 12 can have a variety of sizes, shapes, and configurations. As in this illustrated embodiment, the handle 12 can have a generally elongate cylindrical shape to facilitate grasping thereof by a user's hand or a surgical robot arm. The inner lumen 16a extends through the handle 12 between a proximal end 12p and a distal end 12d thereof. The inner lumen 16a has a substantially constant diameter except at a region where a first engagement feature 18 is located within the handle's inner lumen 16a. A person skilled in the art will appreciate that the handle's lumen 16a may not be precisely constant but nevertheless be considered to be substantially constant for any of a variety of factors, such as manufacturing tolerance and/or sensitivity of measurement equipment. In other embodiments, the handle's inner lumen 16a can be substantially constant in diameter from the proximal end 12p toward the distal end 12d along a substantial portion of the handle 12 and have a smaller diameter near the distal end 12d where the diameter of the inner lumen 16a tapers radially inward. The tapered configuration may facilitate positioning of a suture extending from the shaft 14 into the inner lumen 16a of the handle 12, as discussed further below.

The handle 12 includes one or more irrigation holes 20 formed therein and extending through a sidewall thereof. The irrigation holes 20 extend into the inner lumen 16a such that fluid flowing through the inner lumen 16a, e.g., from the lumen 16b of the shaft 14, can exit out through the irrigation holes 20. Since saline is often delivered under pressure into a joint where an anchor is being implanted using an inserter tool advanced through the lumen 16, the irrigations holes 20 may prevent irrigation fluid from exiting out of the proximal end 12p of the handle 12. Although the handle 12 includes three irrigation holes 20, with two of the irrigation holes 20 being spaced equidistantly around a circumference of the handle 12 at a same axial position (as shown in FIG. 3), the handle 12 can include another number of irrigation holes and, in the case of two or more irrigation holes, can have the irrigation holes spaced at any of a variety of axial and radial positions.

As shown in FIGS. 1 and 2, the handle 12 includes a suture-engaging feature 22 that is configured to releasably engage a suture. In the illustrated embodiment, the suture-engaging feature 22 is in the form of a slit or cleat formed in a proximal facing surface of the proximal end 12p of the handle 12. The suture-engaging feature 22 is configured to allow tension to be maintained on a suture extending through the shaft 14 and the handle 12, with the suture being held in position by the suture-engaging feature 22, e.g., by being crimped in the slit. The suture-engaging feature 22 is recessed in a shallow cut-out formed in the handle's proximal-facing surface, which may help protect the suture engaged by the suture-engaging feature 22 during drilling. The illustrated suture-engaging feature 22 is on the same side as and radially aligned with a longitudinal slot 24 formed in an inner wall 26 of the handle 12 that defines the wall of the inner lumen 16a. The slot 24 is configured to seat the suture therein. The alignment of the suture-engaging feature 22 and the slot 24 may help maintain the suture at a distance apart from a drill passed through the inner lumen 16, and may thus prevent the drill, e.g., a cutting portion at a distal end thereof, from causing damage to the suture. The illustrated slit has an enlarged mouth with sloping sidewalls that merge toward the slit in a direction toward the inner lumen 16a. The enlarged mouth and sloping may facilitate insertion of a suture into the slit. In at least some embodiments, the slit has a width that allows two strands of suture legs to slide therein and to be fixedly and non-slidably maintained. A person skilled in the art will appreciate that the suture-engaging feature 22 can have a variety of other configurations, and need not be in the form of a slit. Also, the suture-engaging feature 22 can be positioned at various other locations on the handle 12 and is not limited to being located on the proximal end 12p of the handle 12 as shown. Exemplary embodiments of suture-engaging features are further described in previously mentioned U.S. Pat. Pub. No. 2016/0310125 entitled "Knotless Suture Anchor Guide" filed Apr. 23, 2015.

As mentioned above, the handle 12 includes a first engagement feature 18 within the handle's inner lumen 16a. The first engagement feature 18 is configured to releasably engage with an engagement feature of an inserter tool, as discussed further below. The first engagement feature 18 is a thread that extends around the inner lumen 16a. In other words, the guide device 16 includes an internal thread in the handle 12. The first engagement feature 18 extends along a partial longitudinal length 16L of the inner lumen 16a that extends through the handle 12, e.g., the inner lumen 16a is only partially threaded. The slot 24 extends through the first engagement feature 18, as shown in FIG. 1, such that the thread is discontinuous. In embodiments of guide devices that do not include a slot, the thread can be continuous. In other embodiments, the first engagement feature 18 can have configurations other than a thread, such as a ratchet or tooth, as discussed further below.

In an exemplary embodiment, as shown in FIG. 1, the first engagement feature 18 is located in a proximal portion of the handle's inner lumen 16a, and hence in a proximal portion of the guide device's inner lumen 16. As also shown in FIG. 1, the first engagement feature 18 can extend to a proximal-most end of the handle's inner lumen 16a, and hence a proximal-most end of the guide device's inner lumen 16, which may facilitate a user's tactile feel and/or audible detection of the first engagement feature's engagement with the inserter tool's engagement feature.

The elongate shaft 14 of the guide device 10 can have a variety of sizes, shapes, and configurations. The elongate shaft 14 has a proximal end 14p that is mated to the distal end 12d of the handle 12 and has a distal end 14d (see FIG. 3) that is configured to be positioned on bone adjacent to an anchor site. The inner lumen 16b extends through the shaft 14 between its proximal and distal ends 12p, 12d. The guide device 16 is thus cannulated, with its inner lumen 16 extending all the way therethrough, e.g., from the proximal end 12p of the handle 12 to the distal end 14d of the shaft 14. The inner lumen 16b has a substantially constant diameter, but can have a varying diameter in other embodiments.

In this illustrated embodiment, the inner lumen 16b of the shaft 14 has a circular cross-sectional shape. In at least some embodiments the shaft 14 is configured such that a cross-sectional shape of its inner lumen 16b is irregular so as to allow both a suture and a drill bit to be passed through the shaft 14 without the drill bit causing any damage to the suture. For example, the inner lumen 16b of the shaft 14 can have an irregular cross-sectional shape such that the shape has a primary region for receiving a drill bit and a secondary offset region for seating the suture. For example, where a circular drill bit is used, the primary region has a generally circular configuration. The secondary offset region is positioned just outside of the primary region so as to define an area extending outside of the diameter where the drill bit is passed through for seating a suture. Exemplary embodiments of shafts with a primary region and a secondary offset region are further described in previously mentioned U.S. Pat. Pub. No. 2016/0310125 entitled "Knotless Suture Anchor Guide" filed Apr. 23, 2015.

As shown in FIG. 3, the shaft's distal end 14d includes at least one bone engaging surface feature 28 configured to engage bone to prevent movement of the guide device 10 relative to the bone. The one or more bone engaging surface features 28 in this illustrated embodiment is in the form of a plurality of teeth extending distally around the circumference of the shaft 14, but the one or more bone engaging surface features 28 can have other configurations, such as a textured surface, etc. The bone-engaging teeth 28 are formed on the distal-facing surface of the shaft 14 so as to be configured to penetrate into bone when the shaft 14 is moved into contact with a bone surface. In other embodiments, the shaft 14 does not have any bone-engaging surface features at its distal end 14d.

As also shown in FIG. 3, the shaft 14 in a distal portion thereof has one or more windows 30 formed therein that are configured to allow viewing through a sidewall of the shaft 14 into the shaft's inner lumen 16b and hence into the guide device's inner lumen 16, such as via a scope or other visualization device being positioned to see through the one or more windows 30. In the illustrated embodiment, the shaft 14 has two windows 30 spaced equidistantly and radially around the shaft 14, although the windows 30 can be at other locations. Each window 30 has a rectangular shape oriented lengthwise along a longitudinal axis of the shaft 14, although the windows 30 can have other shapes, such as generally oblong or oval shaped. In other embodiments, the shaft 14 does not have any windows formed therein.

The guide device 10 is configured to receive therein, e.g., in the inner lumen 16 thereof, a drill configured to drill a hole in bone and is configured to receive therein an inserter tool configured to insert a suture anchor into the hole. The inner lumen 16 can thus have a length that is less than a length of the drill (e.g., less than a length of an elongate shaft of the drill that is advanced through the guide device's inner lumen 16) and less than a length of the inserter tool (e.g., less than a length of an elongate shaft of the inserter tool that is advanced through the guide device's inner lumen 16) to allow each of the drill's distal end and the inserter tool's distal end to exit the guide device 10 and access and enter the bone. As discussed further below, the drill can be inserted into the guide device 10 to form the bone hole and then removed therefrom before the inserter tool is inserted into the guide device 10 to deliver the anchor.

The guide device 10 can be made from any of a variety of materials. In an exemplary embodiment, the guide device 10 is made from a metal (e.g., stainless steel, etc.) or Radel®. Additionally, in an exemplary embodiment, the guide device 10 is configured to be reused, e.g., used on different patients with cleaning and sterilization thereof between uses.

Figure 4:
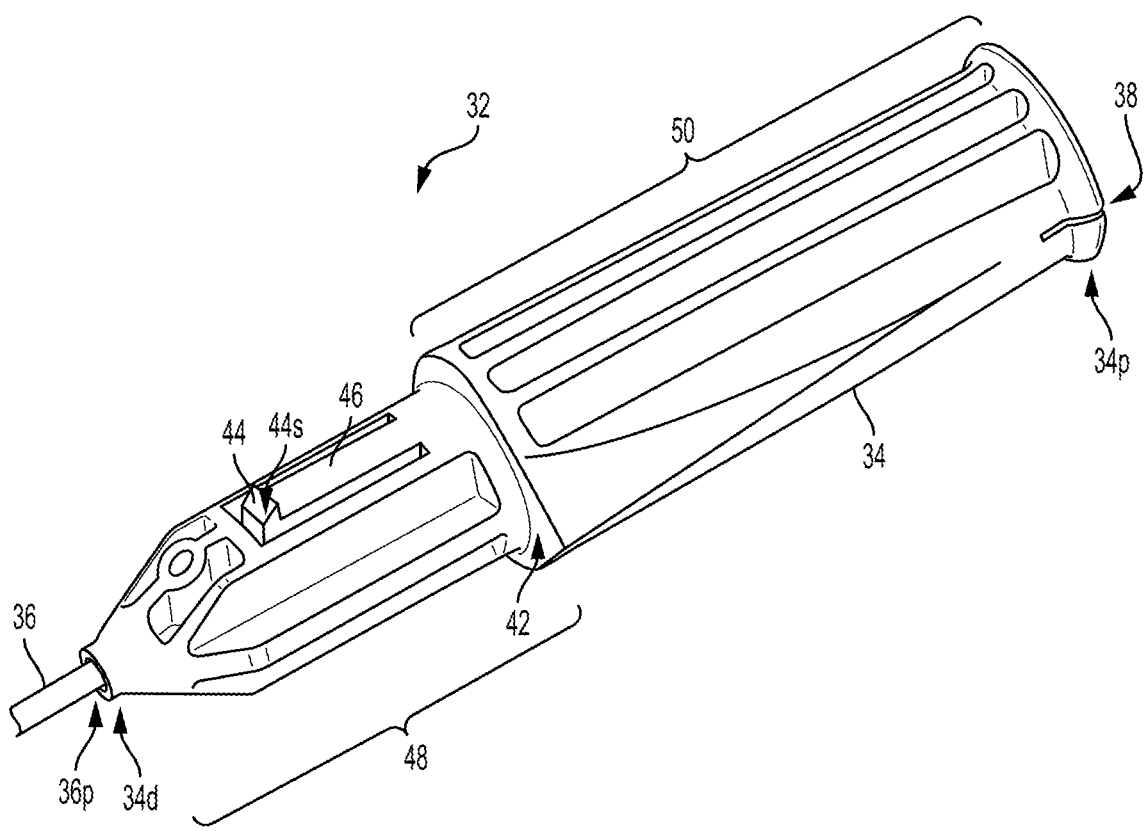
FIG. 4 is a perspective view of a proximal portion of one embodiment of an inserter tool.
Figure 5:
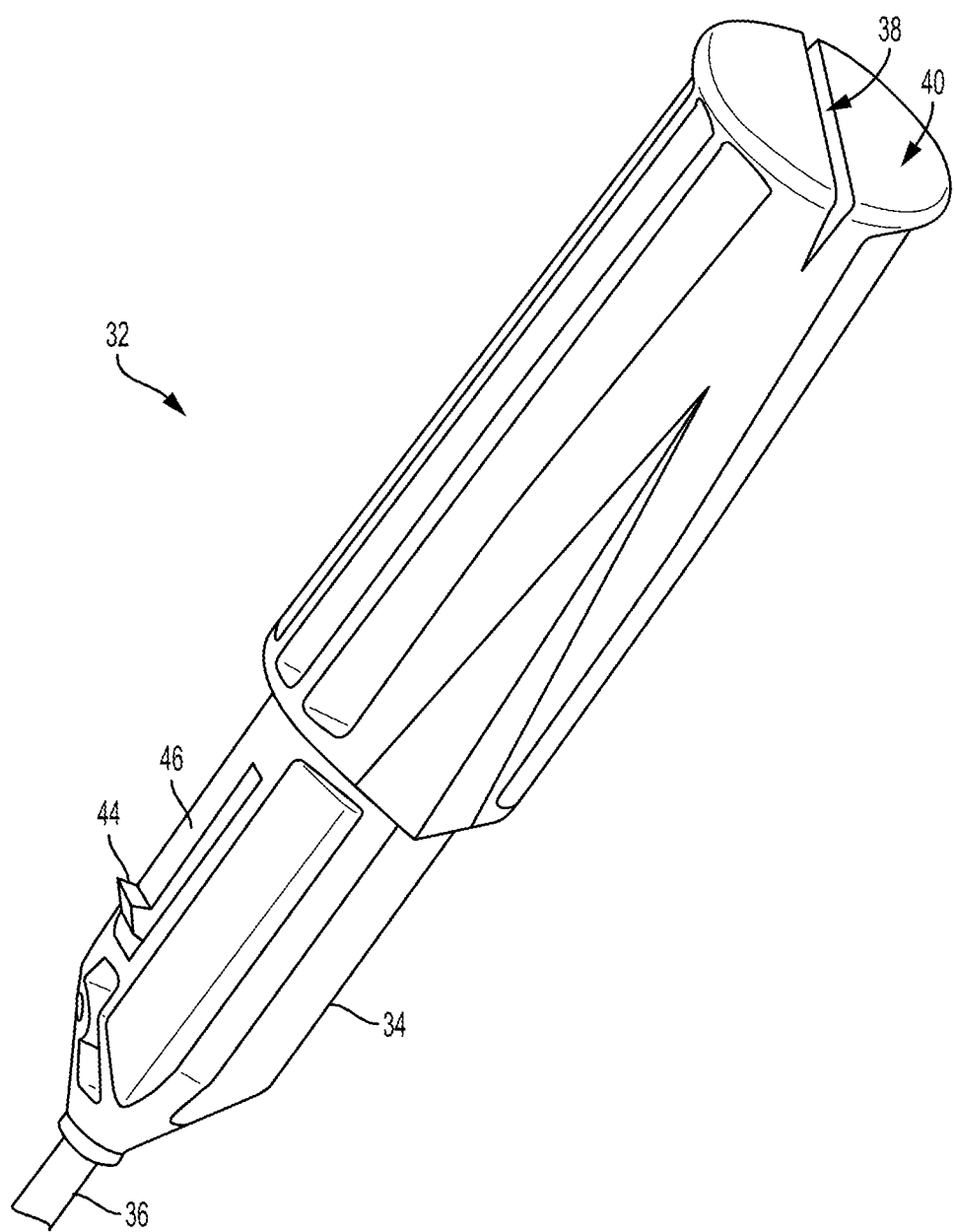
FIG. 5 is a another perspective view of the proximal portion of the inserter tool of FIG. 4.
Figure 6:
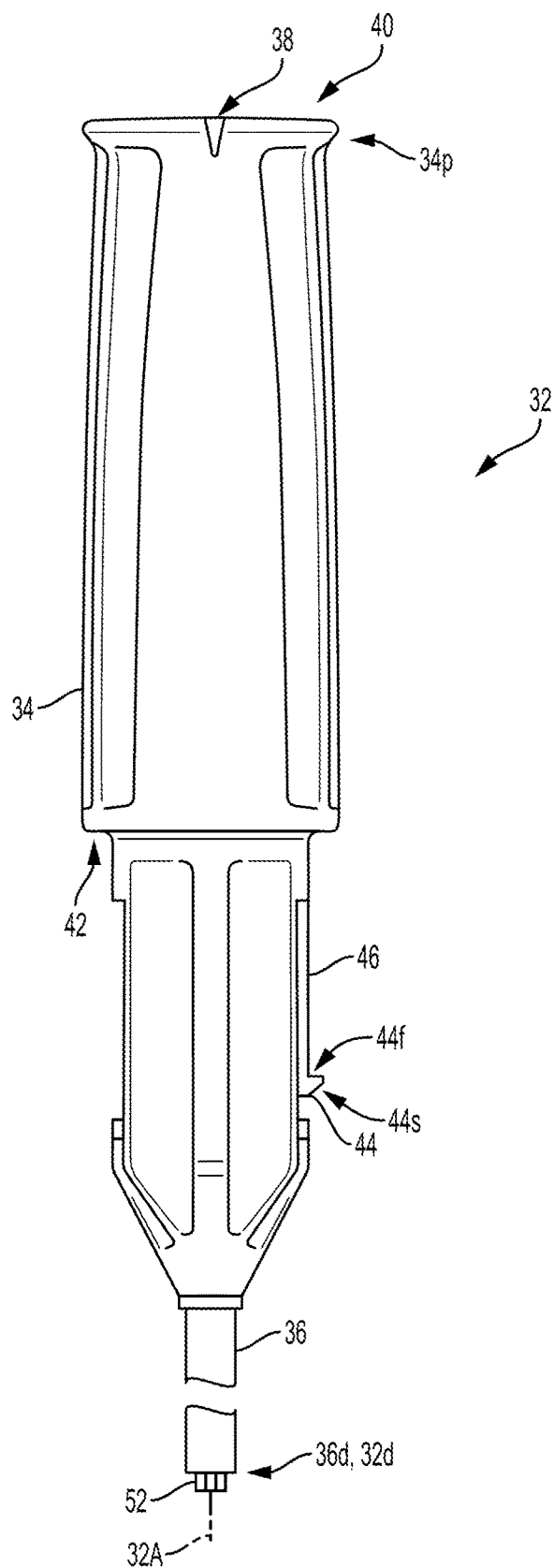
FIG. 6 is a side view of the proximal portion and a distal portion of the inserter tool of FIG. 4.

FIGS. 4-6 illustrate one embodiment of an inserter tool 32 configured to be inserted into a guide device, such as the guide device 10 of FIGS. 1-3. The inserter tool 32 has a handle 34 and an elongate shaft 36 extending distally from the handle 34. The shaft 36 and the handle 34 are longitudinally aligned, but in other embodiments the handle 34 can extend at an angle from the shaft 36, similar to that mentioned above regarding the guide device 10.

The handle 34 can have a variety of sizes, shapes, and configurations. As in this illustrated embodiment, the handle 34 can have a generally elongate cylindrical shape to facilitate grasping thereof by a user's hand or a surgical robot arm.

The handle 34 includes a suture-engaging feature 38 that is configured to releasably engage a suture. The inserter tool's suture-engaging feature 38 is generally configured and used similar to the guide device's suture-engaging feature 22. In the illustrated embodiment, the suture-engaging feature 38 is in the form of a slit or cleat formed in a proximal-facing surface 40 at a proximal end 34p of the handle 34, and hence at a proximal end of the inserter tool 32. The illustrated slit has at each end thereof an enlarged mouth with sloping sidewalls that merge toward the slit in a radially inward direction. As mentioned above, the suture-engaging features 38 can have a variety of configurations other than a slit or cleat and can be positioned at various other locations on the handle 34.

The inserter tool's proximal-facing surface 40 is substantially flat and is configured to be hit with a mallet or other tool to help drive an anchor coupled to a distal end 36d of the elongate shaft 36 (see FIG. 6) into bone. A person skilled in the art will appreciate that the proximal-facing surface 40 may not be precisely flat but nevertheless be considered to be substantially flat for any of a variety of factors, such as manufacturing tolerance and/or sensitivity of measurement equipment. The suture-engaging feature 38 allows the suture therein to be recessed within the handle 34 to protect the suture from being damaged by the mallet or other tool striking the inserter tool 32 on the proximal-facing surface 40.

The handle 34 includes a second engagement feature 44 on an outer surface thereof. The second engagement feature 44 is configured to releasably engage the first engagement feature 18 of the guide device 10, as discussed further below. The second engagement feature 44 is a tooth or ratchet that extends radially outward from the inserter tool 32. The second engagement feature 44 is formed on an end of a spring member 46 configured to flex or spring radially inward to facilitate ratcheting of the tooth 44 along the thread 18 when the inserter tool 32 is translated longitudinally through the guide device's inner lumen 16 in a distal direction. The second engagement feature 44 has a sloped distal-facing surface 44s that slopes upwardly (e.g., proximally), which also facilitates this ratcheting of the tooth 44 by helping the tooth 44 slide over each part of the thread 18 it encounters during the inserter tool's distal translational movement. The second engagement feature 44 also has a substantially flat proximal-facing surface 44f, which is configured to engage the first engagement feature 18 to prevent the inserter tool 32 from moving proximally. In other words, the substantially flat proximal-facing surface 44f can abut against the thread 18 and act as a stop surface that stops the inserter tool 32 from moving proximally within the lumen 16 once the inserter tool 32 has been advanced distally past at least one turn of the thread 18 on the inner wall 26. A tip of the second engagement feature 44 at an interface between the sloped surface 44s and the substantially flat surface 44f is configured to be seated in the thread 18.

The second engagement feature 44 and the spring member 46 are integrally formed with the handle 34, e.g., molded therewith, although in other embodiments the spring member 46 and the second engagement feature 44 can be a separate component and attached to the handle 34, such as by being machined separately from the handle 34 and attached thereto using any of a variety of attachment mechanisms, e.g., welding, adhesive, a hinge, a coil spring, a leaf spring, etc.

The second engagement feature 44 is configured to ratchet downwardly (e.g., distally) along the first engagement feature 18 when the inserter tool 32 is translated distally through the guide device's inner lumen 16. The spring member 46 is configured to allow the second engagement feature 44 to move radially inward as it passes over the protruding portions of the thread 18 so the second engagement feature 44 can sequentially ratchet into each recessed part of the thread 18 that the second engagement feature 44 encounters as it moves distally. The ratcheting of the second engagement feature 44 along the first engagement feature 18 can be configured to cause an audible sound, e.g., a clicking noise, which may help medical personnel using the guide device 10 and inserter tool 32 know that the first and second engagement features 18, 44 are engaged and that the anchor coupled to the inserter tool 32 is in a particular location. The ratcheting of the second engagement feature 44 along the first engagement feature 18 can also be configured to be tactilely felt by a user holding the inserter tool 32 and/or guide device 10 to further help medical personnel. Having two signals (audible and tactile) may allow for redundancy in case one of the signals is missed by the user.

The second engagement feature 44 is also configured to slide within the first engagement feature 18 when the inserter tool 32 is rotated about its longitudinal axis 32A (see FIG. 6) relative to the guide device 10. In other words, the tooth 44 can be in threaded engagement with the thread 18 and slide therein in response to rotation of the inserter tool 32. The rotation of the inserter tool 32 allows the inserter tool 32 to move proximally within the guide device's inner lumen 16 when the first and second engagement features 18, 44 are engaged, with the second engagement feature 44 threading along the first engagement feature 18 in a proximal direction. The inserter tool 32 may thus be removed from the guide device 10 by being rotated relative to the guide device 10 to move proximally out of the guide device 10. After a certain amount of rotation, the second engagement feature 44 will disengage from the first engagement feature 18, e.g., be located proximal thereto, and the inserter tool 32 may finish being removed from the guide device 10 using translational motion in a proximal direction.

The first and second engagement features 18, 44 are configured to cooperate when engaged together to limit movement of the inserter tool 18 to one of two different types of motion depending on whether the inserter tool 32 is moving proximally or distally in the inner lumen 16 of the guide device 10. The first and second engagement features 18, 44 are configured to cooperate when engaged together to limit movement of the inserter tool 18 to a first type of motion, translational or longitudinal motion, when distally advanced through the inner lumen 16. The first and second engagement features 18, 44 are configured to cooperate when engaged together to limit movement of the inserter tool 18 to a second, different type of motion, rotational motion, when proximally advanced through the inner lumen 16. The inserter tool 32 and guide device 10 can thus be configured for foolproof use, with the inserter tool 32 being configured to move in only one way depending on whether the inserter tool 32 is being moved distally or proximally within the inner lumen 16 once the first and second engagement features 18, 44 have become engaged, e.g., once the inserter tool 32 has been advanced distally far enough into the inner lumen 16 for the first and second engagement features 18, 44 to have become engaged. The inserter tool 32, and hence the anchor coupled to a distal end 32d thereof (see FIG. 6), may therefore be prevented from accidentally moving distally or proximally in the inner lumen 16, such as due to the guide device 10 and/or inserter tool 32 being unintentionally jostled by medical personnel or by another device. The anchor may thus be in a predictable location relative to the bone in which it is intended to be implanted, which may help ensure that the anchor is properly implanted and that a suture coupled to the anchor is desirably tensioned before the anchor is fully deployed in the bone, e.g., before the mallet or other tool strikes the inserter tool's proximal-facing surface 40.

Since the anchor coupled to the inserter tool's distal end 32*d* will have been driven into bone before the inserter tool 32 is removed from the guide device 10, as discussed further below, the proximal movement of the inserter tool 32 relative to the guide device 10 will automatically disengage the inserter tool 32 from the anchor, e.g., move the distal end 32*d* proximally out of the anchor, while the anchor remains deployed in bone. Thus, a single motion, e.g., the rotational motion of the inserter tool 32 relative to the guide device 10, can cause both the removal of the inserter tool 32 from the guide device 10 and the release of the anchor from the inserter tool 32. A surgical procedure may thus be performed in less time since one action can accomplish two tasks and/or use of the guide device 10 and inserter tool 32 may be easier for a user to learn since one action can be learned to accomplish two tasks. Further, the one action at this time to accomplish two tasks can be the only possible movement of the inserter tool 32, e.g., the inserter tool 32 can only be rotated to be removed from the guide device 10, so anchor deployment may be assured to happen and to occur in a controlled manner.

In an exemplary embodiment, the second engagement feature 44 is formed in a distal portion 48 of the handle 34 that is configured to be disposed within the inner lumen 16 of the guide device 10. The handle's distal portion 48 has a smaller diameter than the handle's proximal portion 50 at least at an interface between the distal and proximal portions 48, 50. The second engagement feature 44 is formed distal to a distal-facing surface 42 of the inserter tool 32 that is configured to abut against a proximal-facing surface 31 of the guide device 10, e.g., a proximal-facing surface of the handle 12, when the inserter tool 32 is advanced distally through the guide device's inner lumen 16. The guide device's proximal-facing surface 31 and the inserter tool's distal-facing surface 42 are configured to cooperate to stop distal movement of the inserter tool 32 in the inner lumen 16. The second engagement feature 44 is located relative to the inserter tool's stop surface 42 such that the second engagement feature 44 is engaged with the first engagement feature 18 when the inserter tool's distal movement is stopped, e.g., when the surfaces 31, 42 abut one another. In this way, the inserter tool 32 at its distal-most position relative to the guide device 10 is prevented from moving further distally by the engaged stop surfaces 31, 42 and is prevented from moving proximally relative to the guide device 10 by the engaged engagement features 18, 44 until the inserter tool 32 is moved in the second type of motion, e.g., until the inserter tool 32 is rotated about its longitudinal axis 32A relative to the guide device 10 to slide the tooth 44 through the thread 18.

When the first and second engagement features 18, 44 are engaged and when the guide device's proximal-facing surface 31 and the inserter tool's distal-facing surface 42 are abutting one another, a user (or a surgical robot) may hold the guide device 10 and the inserter tool 32 with confidence that the inserter tool 32, and hence the suture anchor coupled thereto, will not move relative to the guide device 10 until intentionally manipulated to do so. Because the inserter tool 32 is prevented from moving proximally or distally relative to the guide device 10 when the first and second engagement features 18, 44 are engaged and when the guide device's proximal-facing surface 31 and the inserter tool's distal-facing surface 42 are abutting one another, a user may hold the guide device 10 and the inserter tool 32 with one hand without risking accidental movement of the inserter tool 32, and hence the suture anchor coupled thereto. The user's hand may thus be free to perform other tasks. Similarly, because the inserter tool 32 is prevented from moving proximally or distally relative to the guide device 10 when the first and second engagement features 18, 44 are engaged and when the guide device's proximal-facing surface 31 and the inserter tool's distal-facing surface 42 are abutting one another, a single surgical robot arm may be used to hold the guide device 10 and inserter tool 32 as a unit.

In an exemplary embodiment, when the surfaces 31, 42 abut one another, the second engagement feature 44 is located proximal to a distal-most end of the first engagement feature 18. In other words, the second engagement feature 44 is located in an intermediate portion of the first engagement feature 18 along its longitudinal length 16L. In this way, when the inserter tool 32 is hit with a mallet or other tool to urge the anchor at the distal end 32*d* of the inserter tool 32 into bone, the second engagement feature 44 can remain engaged with the first engagement feature 18 when the inserter tool 32 is hit to move distally. The longitudinal length 16L along which the first engagement feature 18 extends can therefore be greater than a longitudinal length of the anchor to ensure that the first and second engagement features 18, 44 are engaged from just before the anchor enters a hole in the bone against which the distal end 14*d* of the guide device's elongate shaft 14 contacts until the anchor is fully disposed within the hole and the inserter tool 32 is ready to be removed from the guide device 10 and the patient. The audible and tactile signals may thus signal to medical personnel when the anchor is just about to enter the bone hole and is then being advanced therein.

In an exemplary embodiment, when the surfaces 31, 42 abut one another, the anchor coupled to the distal end 32*d* of the inserter tool 32 is disposed with a hole in the bone against which the distal end 14*d* of the guide device's elongate shaft 14 contacts. The surfaces 31, 42 abutting one another may thus allow medical personnel to know that the anchor is in position to be fully driven into the bone hole via force applied to the inserter tool 32, e.g., hitting the mallet or other tool on the inserter tool's proximal-facing surface 40. In other words, a distance that the inserter tool 32 is advanced into the guide device 10 can define a depth of the anchor's deployment in bone. The guide device 10 and the inserter tool 32 may therefore be configured to cooperate to indicate to medical personnel that the anchor is in a desired, predictable position relative to the bone.

The distal-facing surface 42 of the inserter tool 32 and the proximal-facing surface 31 of the guide device 10 have a corresponding shape, which may facilitate alignment of the inserter tool 32 and the guide device 10. The inserter tool 32 and the guide device 10 being aligned may help a suture extending through the guide device's inner lumen 16 engage the inserter tool's suture-engaging feature 38 at a convenient approach angle that helps prevent the suture from tangling or being obstructive to holding of the inserter tool 32. In an exemplary embodiment, the corresponding shape of the surfaces 31, 42 is a shape that has only one relative orientation in which they are aligned, such as in the illustrated embodiment in which the surfaces 31, 42 have a teardrop shape in which there is a single orientation relative to one another in which the teardrop shapes will be aligned, e.g., with the pointed tips of the teardrops aligned.

Figure 7:
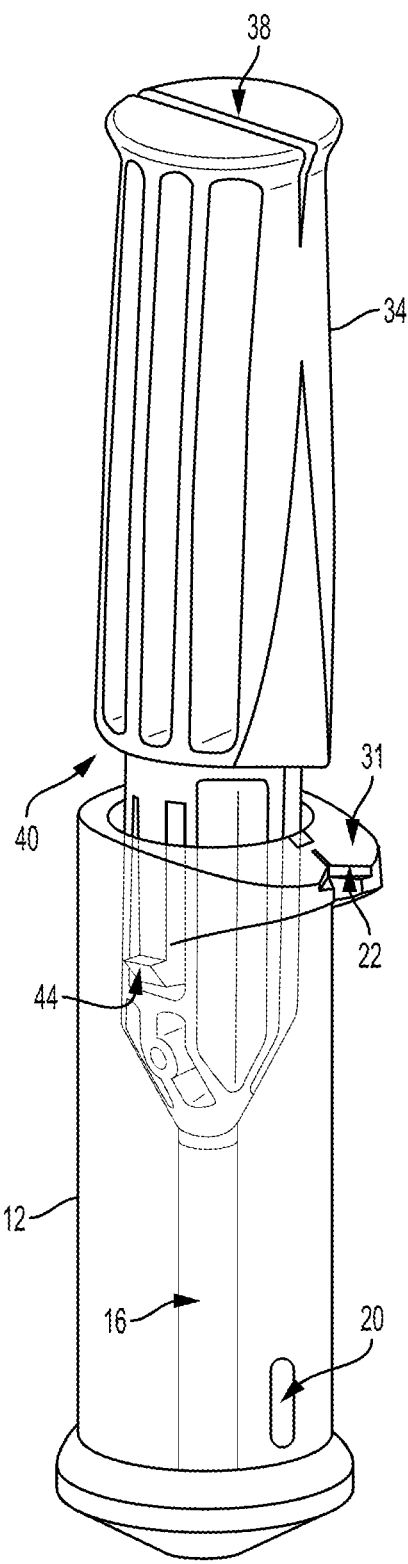
FIG. 7 is a transparent perspective view of the inserter tool of FIG. 4 partially distally advanced into the guide device of FIG. 1.
Figure 8:
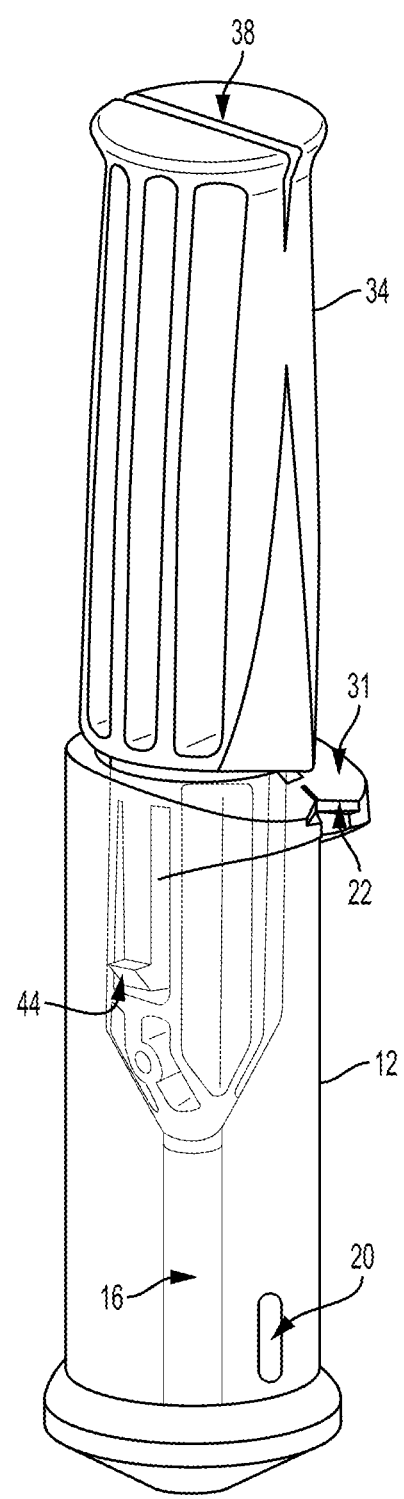
FIG. 8 is a transparent perspective view of the inserter tool of FIG. 7 fully distally advanced into the guide device of FIG. 7.

FIG. 7 illustrates the inserter tool 32 advanced distally into the guide device 10 (with the elongate shafts 14, 36 and the first engagement feature 18 omitted for clarity of illustration) prior to abutment of the distal-facing surface 42 of the inserter tool 32 and the proximal-facing surface 31 of the guide device 10. FIG. 8 illustrates the inserter tool 32 advanced distally from its position in FIG. 7 with the surfaces 31, 42 now abutting such that the inserter tool 32 is in its distal-most position relative to the guide device 10. As shown in FIG. 8, the cross-sectional shapes of the surfaces 31, 42 are aligned such that a suture seated in the guide device's slot 24 and extending proximally therefrom can extend proximally to the inserter tool's suture-engaging feature 38 in a substantially straight line along an exterior of the inserter tool's handle 34 from the slot 24 to the suture-engaging feature 38. A person skilled in the art will appreciate that the suture may not extend along a precisely straight line but nevertheless be considered to extend in a substantially straight line due to any number of factors, such as flexibility of the suture and sensitivity of measurement devices.

In other embodiments, the second engagement feature 44 of the inserter tool 32 can have configurations other than a ratchet or tooth, such as a thread. For example, the first engagement feature of the guide device can be a ratchet or tooth that extends radially inward from an inner surface of the guide device, e.g., radially inward from the inner wall that defines the inner lumen in the guide device's handle, and the second engagement feature of the inserter tool can be a thread configured to engage the ratchet or tooth. In this configuration, when the first and second engagement features are engaged, the inserter tool is configured to move distally in the guide device's inner lumen by being rotated about a longitudinal axis of the inserter tool and is configured to move proximally in the guide device's inner lumen by being translated longitudinally in a proximal direction. The tooth would have its slope opposite to that in the illustrated embodiment of the tooth 44 of FIGS. 4-6, e.g., slope down in a distal direction, to allow for this proximal translation. In such an embodiment, the guide device can include a spring member attached to the ratchet or tooth to facilitate ratcheting thereof along the thread.

Figure 9:
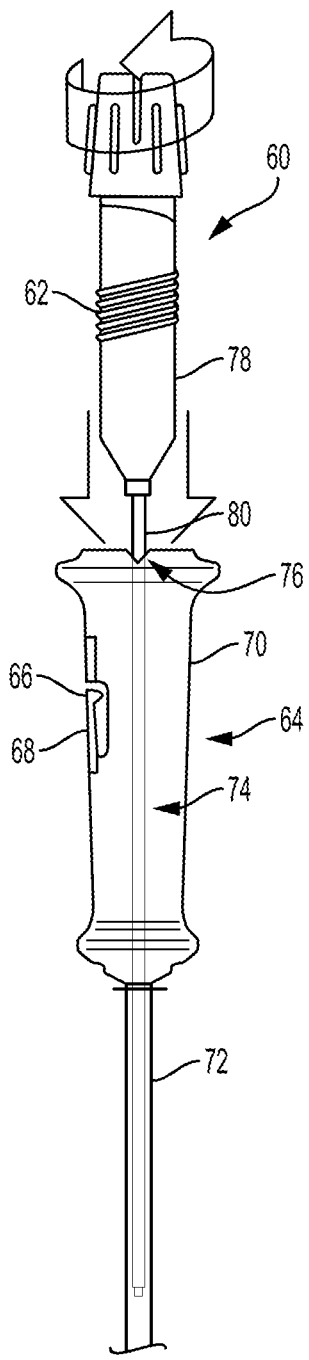
FIG. 9 is a side, partially transparent view of another embodiment of an inserter tool partially advanced into another embodiment of a guide device.

FIG. 9 illustrates one embodiment of an inserter tool 60 that has a second engagement feature 62 in the form of a thread and that is configured to be received in a guide device 64 having a first engagement feature 66 in the form of a ratchet or tooth that extends into an inner lumen 74 of the guide device 64. The guide device 64 thus includes a spring member 68. The guide device 64 is otherwise generally configured and used similar to the guide device 10 of FIGS. 1-3, e.g., includes a handle 70, an elongate shaft 72 extending distally from the handle 70, an inner lumen 74 extending through the guide device 64, and a suture-engaging feature 76. The inserter tool 60 is generally configured and used similar to the inserter tool 32 of FIGS. 4-6, e.g., includes a handle 78 and an elongate shaft 80 extending distally from the handle 78. The inserter tool 60 is configured to be advanced into the guide device's inner lumen 74 by being longitudinally translated therein in a distal direction, with the first and second engagement features 66, 62 becoming engaged with one another. The inserter tool 60 is configured to be removed from the guide device 64 by rotating the inserter tool 60 to advance the inserter tool 60 proximally out of the guide device 64.

Figure 10:
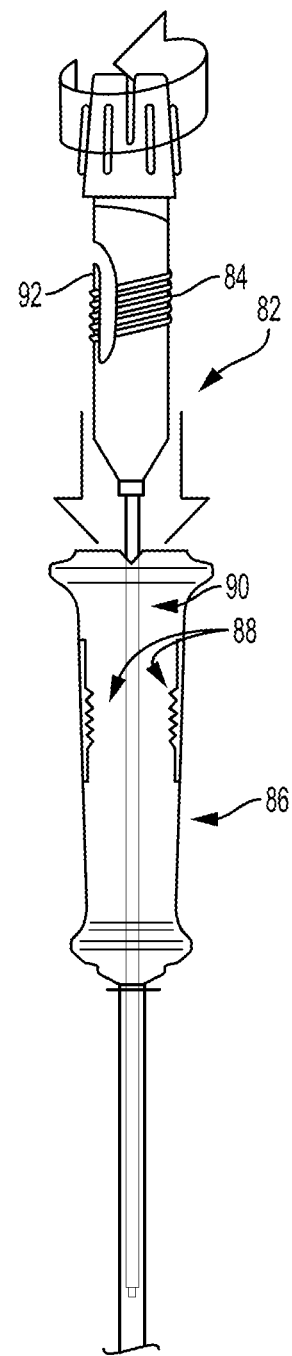
FIG. 10 is a side, partially transparent view of yet another embodiment of an inserter tool partially advanced into yet another embodiment of a guide device.

FIG. 10 illustrates one embodiment of an inserter tool 82 that is generally configured and used similar to the inserter tool 32 of FIGS. 4-6 except that it has a second engagement feature 84 in the form of a thread. The inserter tool 82 is configured to be received in a guide device 86 having a first engagement feature 88 in the form of a ratchet or tooth. The guide device 86 is generally configured and used similar to the guide device 10 of FIGS. 1-3. The inserter tool 82 is configured to be advanced into the guide device's inner lumen 90 by being longitudinally translated therein in a distal direction, with the first and second engagement features 88, 84 becoming engaged with one another. The inserter tool 82 includes a spring member 92, which has the second engagement feature 84 formed thereon, that springs as the second engagement feature 84 ratchets down the first engagement feature 84. The inserter tool 82 is configured to be removed from the guide device 86 by rotating the inserter tool 82 to advance the inserter tool 82 proximally out of the guide device 86.

FIG. 11 illustrates another embodiment of an inserter tool 94 that is generally configured and used similar to the inserter tool 82 of FIG. 10 except that its second engagement feature 96 in the form of a thread extends only partially, instead of fully, around a circumference of the inserter tool 94. In this illustrated embodiment, the thread extends around about 30% of the inserter tool's circumference. A person skilled in the art will appreciate that a value may not be precisely at that value but nevertheless be considered to be at about that value due to any number of factors, such as manufacturing tolerance and sensitivity of measurement devices. The inserter tool 94 is configured to be received in a guide device 96. The guide device 96 is generally configured and used similar to the guide device 10 of FIGS. 1-3. The guide device 96 has a first engagement feature 98 in the form of a ratchet or tooth extending radially inward from a sidewall thereof. As also shown in FIG. 11A, the guide device 96 also has an opening 99 formed in the sidewall at a location that is axially aligned with the first engagement feature 98. The inserter tool 94 is configured to be advanced into the guide device's inner lumen 97 by being longitudinally translated therein in a distal direction, with the first and second engagement features 98, 96 becoming engaged with one another with the first engagement feature 98 ratcheting along the second engagement feature 96 while the inserter tool's spring member 95 springs. The inserter tool 94 is configured to be removed from the guide device 96 by rotating the inserter tool 94 until the first and second engagement features 98, 96 disengage by the second engagement feature 96 being fully advanced into the opening 99. The opening 99 can thus extend around about 30% of the guide device's circumference to match the second engagement feature's extension around the inserter tool's circumference. With the second engagement feature 98 positioned in the opening 99, the inserter tool 82 can be pulled proximally with longitudinal motion out of the guide device 96.

FIG. 12 illustrates another embodiment of an inserter tool 93 that has a second engagement feature 91 in the form of a thread and that is configured to be received in a guide device, such as the guide device 64 of FIG. 9. The inserter tool 93 is generally configured and used similar to the inserter tool 94 of FIG. 11, except that the second engagement feature 91 extends around about 70% of the inserter tool's circumference and the inserter tool does not include a spring member. The inserter tool 93 is configured to be advanced into the guide device's inner lumen 74 by being longitudinally translated therein in a distal direction, with the first and second engagement features 91, 66 becoming engaged with one another with the first engagement feature 91 ratcheting along the second engagement feature 91 while guide device's spring member 68 springs. The inserter tool 93 is configured to be removed from the guide device 64 by rotating the inserter tool 94 until the first and second engagement features 91, 66 disengage by the first engagement feature 66 encountering the portion of the inserter tool's circumference that does not have the thread 91 formed thereon. The inserter tool 93 can then be pulled proximally with longitudinal motion out of the guide device 64.

In other embodiments, the second engagement feature an inserter tool can have configurations other than a ratchet or tooth and other than a thread. FIGS. 13-16 illustrate one embodiment of an inserter tool 1700 that has a second engagement feature 1702 in the form of a protrusion or bump and that is configured to be received in a guide device 1704 having a first engagement feature 1706, 1706a in the form of a tapered groove or channel formed in an inner wall thereof. For clarity of illustration, FIGS. 14 and 16 only show the second engagement feature 1702 of the inserter tool 1700. The inserter tool 1700 is generally configured and used similar to the inserter tool 32 of FIGS. 4-6, e.g., includes a handle 1710 and an elongate shaft 1712 extending distally from the handle 1708. The guide device 1704 is generally configured and used similar to the guide device 10 of FIGS. 1-3, e.g., includes a handle 1708, an elongate shaft 1714 extending distally from the handle 1708, an inner lumen 1716 extending through the guide device 1704, and a suture-engaging feature 1718. The inserter tool 1700 is configured to be advanced into the guide device's inner lumen 1716 via longitudinal translation by aligning the second engagement feature 1702 with a wider open proximal mouth of the first engagement feature 1706 and longitudinally translating the second engagement feature 1702 through the first engagement feature 1706 in a distal direction until the second engagement feature 1702 is distally beyond the first engagement feature 1706. The inserter tool 1700 is then rotated to misalign the first and second engagement features 1706, 1702. The inserter tool 1700 is configured to be removed from the guide device 1704 by rotating the inserter tool 1700 so the first and second engagement features 1706, 1702 again align, then the inserter tool 1700 can be advanced proximally out of the guide device 1704 via longitudinal translation.

Figure 13:
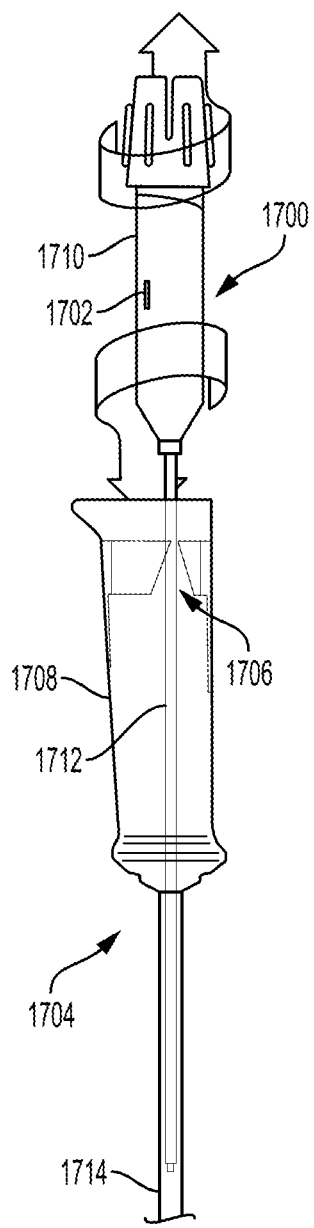
FIG. 13 is a side, partially transparent view of yet another embodiment of an inserter tool partially advanced into yet another embodiment of a guide device.
Figure 14:
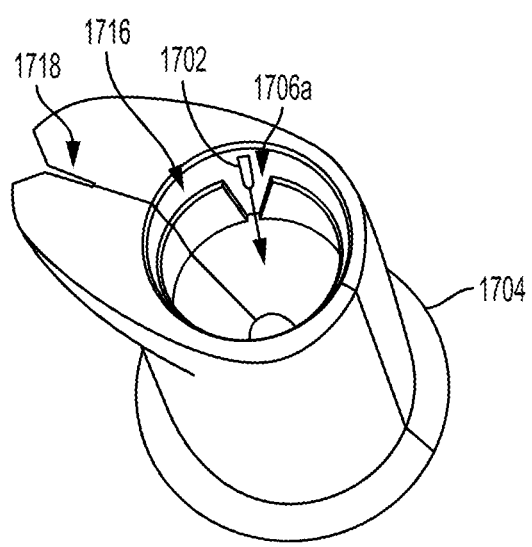
FIG. 14 is a perspective view of the guide device of FIG. 13 and a portion of the inserter tool of FIG. 13.
Figure 15:
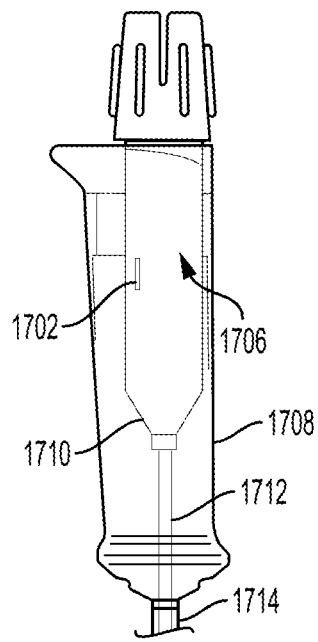
FIG. 15 is a side, partially transparent view of the inserter tool of FIG. 13 advanced fully into the guide device of FIG. 13.
Figure 16:
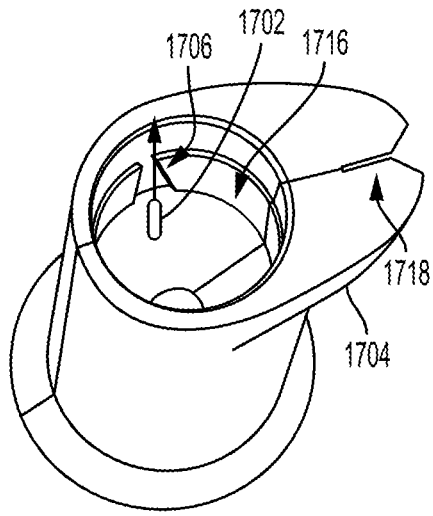
FIG. 16 is another perspective view of the guide device of FIG. 13 and a portion of the inserter tool of FIG. 13.

The guide device 1704 includes two tapered grooves or channels 1706, 1706a formed in an inner wall thereof, with one 1706 tapering as shown in FIGS. 13 and 16 and the other 1706a tapering as in FIG. 14. The inserter tool 1700 can be configured to be advanced into the guide device 1704 with the second engagement feature 1702 distally advancing into the tapered groove or channel 1706 having the wider open proximal mouth, as illustrated in FIGS. 13 and 14, and then subsequently proximally advancing into the other tapered groove or channel 1706a having the wider open distal mouth, as illustrated in FIG. 16.

Figure 16A:
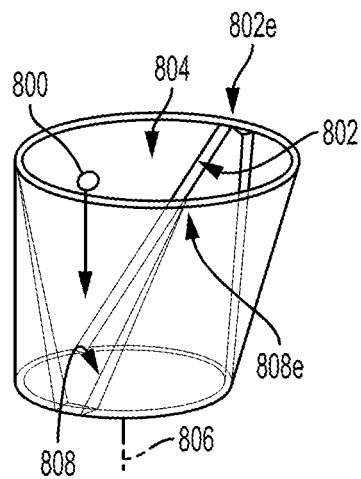
FIG. 16A is a perspective transparent view of a proximal portion of another embodiment of a guide device and an engagement feature of an inserter tool.

FIG. 16A illustrates another embodiment of engagement features 800, 802 of an inserter tool and guide device, respectively. The second engagement feature of the inserter tool is in the form of a protrusion or bump, in this illustrated embodiment a rounded bump instead of the elongated ridge of the inserter tool 1700 of FIG. 13. The guide device has the alignment feature 802 on an inner wall of the guide device's handle that defines a portion of the guide device's inner lumen 804 that extends therethrough. The guide device's engagement feature 802 is in the form of a groove or channel formed in the inner wall. The groove or channel is angled relative to a longitudinal axis 806 of the guide device. The inserter tool's engagement feature 800 is configured to slidably engage the groove or channel. The inserter tool is configured to be advanced into the guide device via rotational motion, with the inserter tool's engagement feature 800 being advanced through an open end 802e of the guide device's engagement feature 802. The inserter tool's alignment feature 800 then slides distally down the groove or channel 802 as the inserter tool rotates about the longitudinal axis 806. In this way, the inserter tool is aligned in a predetermined position relative to the guide device, which may help ensure that suture-engaging features of the guide device and inserter tool are aligned and/or that first and second engagement features of the guide device and inserter tool engage one another.

To remove the inserter tool from the guide device, the inserter tool can be rotated about the longitudinal axis 806 in a same direction that the inserter tool was rotated to slide the inserter tool's engagement feature 800 distally down the groove or channel 802. The inserter tool's engagement feature 800 will thus disengage from the groove or channel 802, allowing the inserter tool to be pulled in a proximal direction and longitudinally translate out of the guide device. Alternatively, the inserter tool can be rotated about the longitudinal axis 806 until the inserter tool's engagement feature 800 engages with a second groove or channel 808 formed in the inner wall. The inserter tool's continued rotation in the same direction will slide the inserter tool's engagement feature 800 upward or proximally along the second groove or channel 808 and exit therefrom through the second groove or channel's open end 808e, thereby allowing release of the inserter tool from the guide device. In this illustrated embodiment the grooves or channels 802, 808 are interchangeable, e.g., the inserter tool's engagement feature 800 can instead slide distally down the second groove or channel 808 and slide proximally up the other groove or channel 802.

FIGS. 17-18 and 20-21 illustrate another embodiment of an inserter tool 100 configured to be inserted into a guide device, such as the guide device 102 shown in FIGS. 19-21. The inserter tool 100 is generally configured and used similar to the inserter tool 32 of FIGS. 4-6, e.g., includes a handle 104, an elongate shaft 106 extending distally from the handle 104, and a second engagement feature 108. The guide device 102 is configured and used similar to the guide device 10 of FIGS. 1-3, e.g., includes a handle 110, an elongate shaft 112 extending distally from the handle 110, an inner lumen 122 extending through the guide device 102, and a first engagement feature (obscured in FIGS. 19-21) extending radially inward from an inner wall that defines the guide device's inner lumen 122. The second engagement feature 108 is a thread, and the first engagement feature is a ratchet or tooth. The second engagement feature 108 is formed on a spring member 114 configured to flex or spring radially inward to facilitate ratcheting of the first engagement feature along the second engagement feature 108 when the inserter tool 100 is translated longitudinally through the guide device's inner lumen 122 in a distal direction, similar to the spring member 46 discussed above. The first engagement feature has a width greater than a width of the longitudinally-extending spaces on either side of the spring member 114 so the first engagement feature can remain engaged with the thread 108 when the inserter tool 100 is rotated about its longitudinal axis when inside the inner lumen 122 to remove the inserter tool 100 from the guide device 102. The inserter tool 100 and the guide device 102 also each include a suture-engaging feature 116, 118 similar to the suture-engaging features 22, 38 discussed above. In the illustrated embodiment, the inserter tool's suture-engaging feature 116 is a wedge or protrusion configured to have a suture wrapped therearound, and the guide device's suture-engaging feature 118 is a slit or cleat. The guide device 102 also includes one or more irrigation holes 120 similar to the one or more irrigation holes 20 discussed above.

Figure 22:
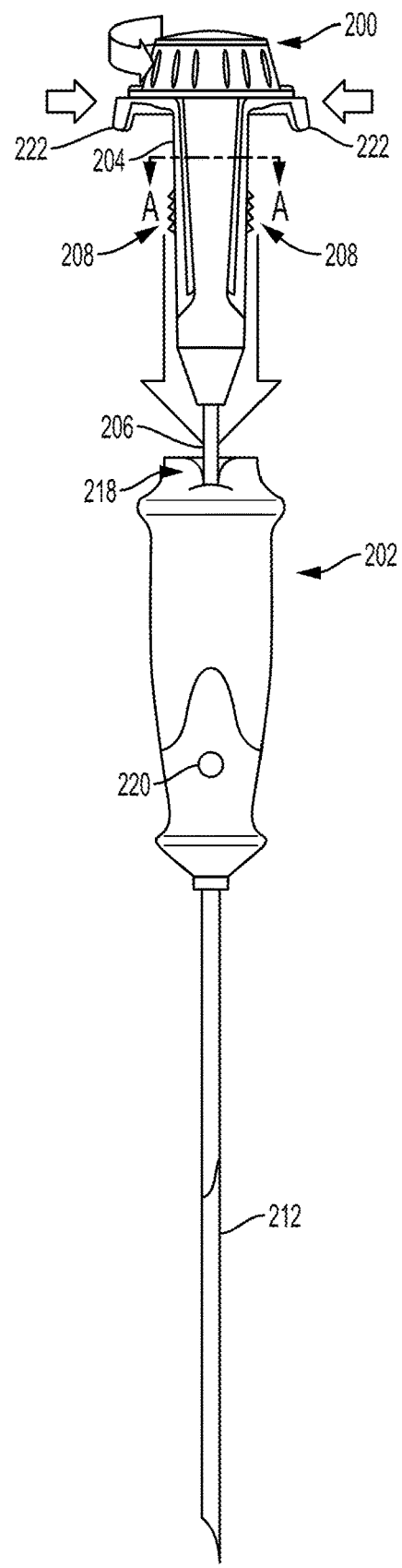
FIG. 22 is a side view of another embodiment of an inserter tool partially distally advanced into another embodiment of a guide device.
Figure 23:
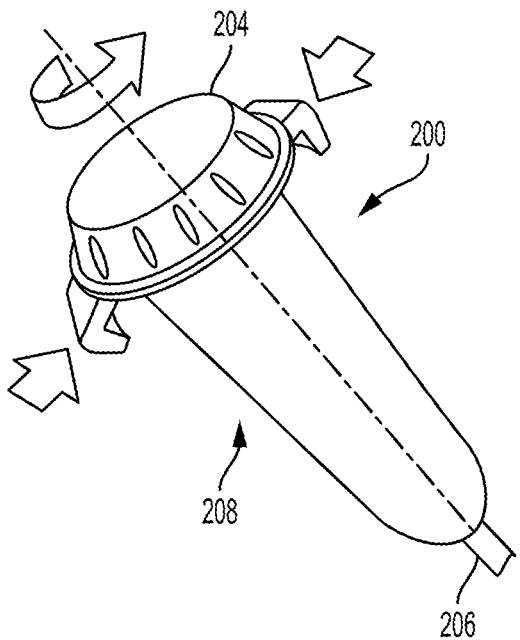
FIG. 23 is a perspective view of a proximal portion of the inserter tool of FIG. 22.
Figure 24:
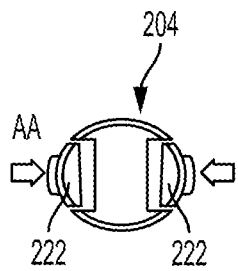
FIG. 24 is a cross-sectional view of the inserter tool of FIG. 22.
Figure 25:
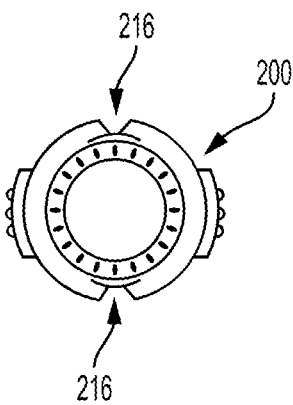
FIG. 25 is a top view of the inserter tool of FIG. 22.

FIGS. 22-25 illustrate another embodiment of an inserter tool 200 configured to be inserted into a guide device, such as the guide device 202 shown in FIGS. 22-23. The inserter tool 200 is generally configured and used similar to the inserter tool 32 of FIGS. 4-6, e.g., includes a handle 204, an elongate shaft 206 extending distally from the handle 204, a suture-engaging feature 216 in the form of a pair of slits or cleats, and a second engagement feature 208, which is a thread similar to the second engagement feature 108 discussed above. The guide device 202 is configured and used similar to the guide device 10 of FIGS. 1-3, e.g., includes a handle 210, an elongate shaft 212 extending distally from the handle 210, an inner lumen extending through the guide device 202, a suture-engaging feature 218 in the form of a pair of slits or cleats, one or more irrigation holes 220, and a first engagement feature (obscured in FIGS. 22-23) in the form of a tooth or ratchet extending radially inward from an inner wall that defines the guide device's inner lumen similar to that of the guide device 102 discussed above.

In this illustrated embodiment, the first engagement feature includes a pair of teeth or ratchets, and the second engagement feature 208 includes two threaded portions each formed on a spring member 214 configured to flex or spring radially inward to facilitate ratcheting of the first engagement feature along the second engagement feature 208 when the inserter tool 200 is translated longitudinally through the guide device's inner lumen in a distal direction, similar to the spring member 46 discussed above. The inserter tool 200 can be removed proximally from the guide device 202 by being rotated about the inserter tool's longitudinal axis, similar to that discussed above.

The inserter tool 200 also includes a quick release feature that allows the inserter tool 200 to be removed proximally from the guide device 202 without rotation thereof when the first and second engagement features are engaged with one another. The quick release feature is in the form of a pair of tabs 222 each operatively associated with one of the spring members 214 and hence with one of the threaded portions. The tabs 222 are configured to be pressed radially inward, thereby causing the spring members 214 and the threaded portions thereon to move radially inward. The second engagement feature 208 thus moves inwardly, allowing the first engagement feature to become disengaged therefrom to allow the inserter tool 200 to be pulled proximally to translate longitudinally through and out of the guide device 202. The quick release feature may save time during a surgical procedure and/or facilitate safety.

In this illustrated embodiment, the thread 208 extends only partially around the inserter tool handle's circumference, in contrast to, for example, the thread 108 of the inserter tool 100 of FIG. 8 that extends around a full circumference of the inserter tool's handle 104. Thus, rotating the inserter tool 200 within the guide device 202 can slide the guide device's first engagement feature along the thread 208 and then release the engagement of the thread 208 and the guide device's first engagement feature when the guide device's first engagement feature reaches an unthreaded portion around the inserter tool's circumference. At this point, with the disengagement of the first and second engagement features, the inserter tool 200 can be removed from the guide device 202 via longitudinal translation, e.g., pulling the inserter tool 200 in a proximal direction.

Figure 26:
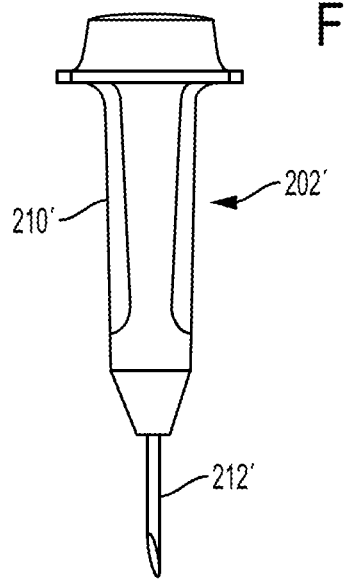
FIG. 26 is a side view of one embodiment of an obturator.

FIG. 26 illustrates one embodiment of an obturator 202' through which an inserter tool and guide device, such as the inserter tool 200 and guide device 202 of FIG. 22 or other inserter tools and guide devices described herein, can be advanced to enter a body of a patient. The obturator 202' includes a handle 210', an elongate shaft 212' extending distally from the handle 210, and an inner passageway extending through the handle 210' and shaft 212' through which the inserter tool and guide device can be advanced.

FIGS. 27-28 illustrate another embodiment of an inserter tool 300 configured to be inserted into a guide device, such as the guide device 302 shown in FIG. 28. The inserter tool 300 is generally configured and used similar to the inserter tool 32 of FIGS. 4-6, e.g., includes a handle 304, an elongate shaft 306 extending distally from the handle 304, a suture-engaging feature 316 in the form of a slit or cleat extending along the handle's proximal-facing surface, and a second engagement feature 308, which is a thread similar to the second engagement feature 108 discussed above. The inserter tool 300 also includes a quick release feature in the form of a pair of tabs 322, similar to the tabs 222 discussed above, that allows the inserter tool 300 to be removed proximally from the guide device 302 without rotation thereof. The guide device 302 is configured and used similar to the guide device 10 of FIGS. 1-3, e.g., includes a handle 310, an elongate shaft 312 extending distally from the handle 310, an inner lumen extending through the guide device 302, a suture-engaging feature 318 in the form of a pair of slits or cleats, one or more irrigation holes 320, and a first engagement feature (obscured in FIG. 28) in the form of a tooth or ratchet extending radially inward from an inner wall that defines the guide device's inner lumen similar to that of the guide device 102 discussed above.

Figure 29:
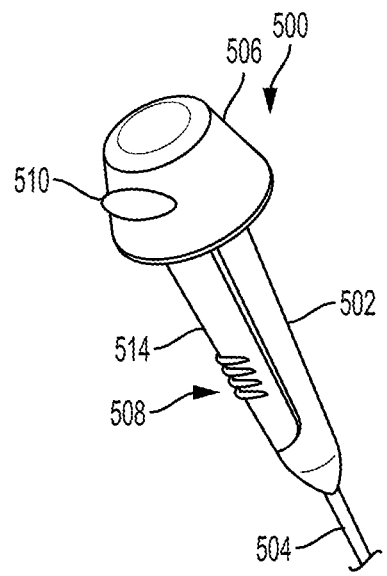
FIG. 29 is a perspective view of a proximal portion of another embodiment of an inserter tool.
Figure 30:
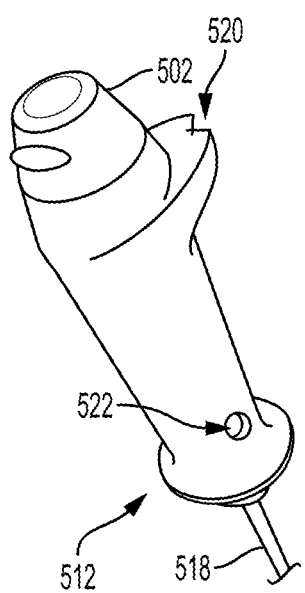
FIG. 30 is a perspective view of the inserter tool of FIG. 29 fully distally advanced into another embodiment of a guide device.
Figure 31:
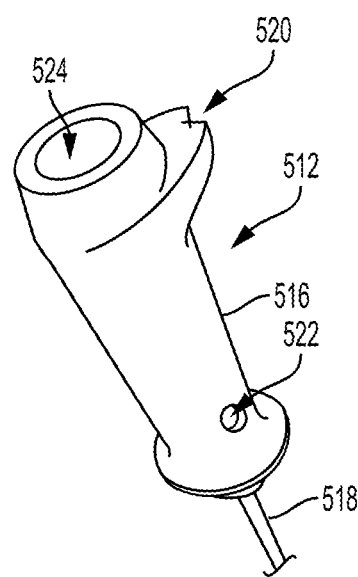
FIG. 31 is a perspective view of a proximal portion of the guide device of FIG. 30.

FIGS. 29-30 illustrate another embodiment of an inserter tool 500 configured to be inserted into a guide device, such as the guide device 512 shown in FIGS. 30-31. The inserter tool 500 is generally configured and used similar to the inserter tool 32 of FIGS. 4-6, e.g., includes a handle 502, an elongate shaft 504 extending distally from the handle 502, a suture-engaging feature 506 in the form of a slit or cleat, and a second engagement feature 508, which is a thread on a spring member 514 similar to the second engagement feature 108 discussed above. The thread 508 is only on one side of the inserter tool 500 but is otherwise similar to the inserter tool 200 of FIG. 22 and the inserter tool 300 of FIG. 27 that each have two threaded portions and two spring members. The inserter tool 500 also includes a quick release feature in the form of a button or tab 510, similar to the tabs 222 discussed above, that allows the inserter tool 500 to be removed proximally from the guide device 512 without rotation thereof. The guide device 512 is configured and used similar to the guide device 10 of FIGS. 1-3, e.g., includes a handle 516, an elongate shaft 518 extending distally from the handle 516, an inner lumen 524 extending through the guide device 512, a suture-engaging feature 520 in the form of a slit or cleat, one or more irrigation holes 522, and a first engagement feature (obscured in FIGS. 30-31) in the form of a tooth or ratchet extending radially inward from an inner wall that defines the guide device's inner lumen 524 similar to that of the guide device 102 discussed above.

Figure 32:
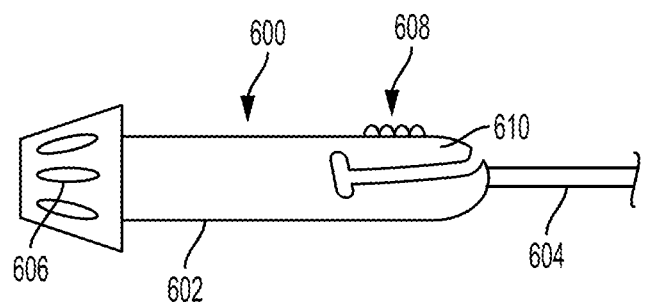
FIG. 32 is a side view of a proximal portion of another embodiment of an inserter tool.

FIG. 32 illustrates another embodiment of an inserter tool 600 configured to be inserted into a guide device. The inserter tool 600 is generally configured and used similar to the inserter tool 32 of FIGS. 4-6, e.g., includes a handle 602, an elongate shaft 604 extending distally from the handle 602, a suture-engaging feature 606 in the form of a wedge or protrusion, and a second engagement feature 608, which is a thread on a spring member 610 similar to the second engagement feature 108 discussed above. The spring member 610 is at a distal end of the inserter tool 600, hence the second engagement feature 608 is in a distal portion of the inserter tool 600. The corresponding first engagement feature of the guide device in which the inserter tool 600 is inserted is therefore located more distally in the guide device's handle than when the inserter tool's second engagement feature is in a proximal portion of the inserter tool. The thread 608 is only on one side of the inserter tool 600 but is otherwise similar to the inserter tool 200 of FIG. 22 and the inserter tool 300 of FIG. 27 that each have two threaded portions and two spring members.

Figure 33:
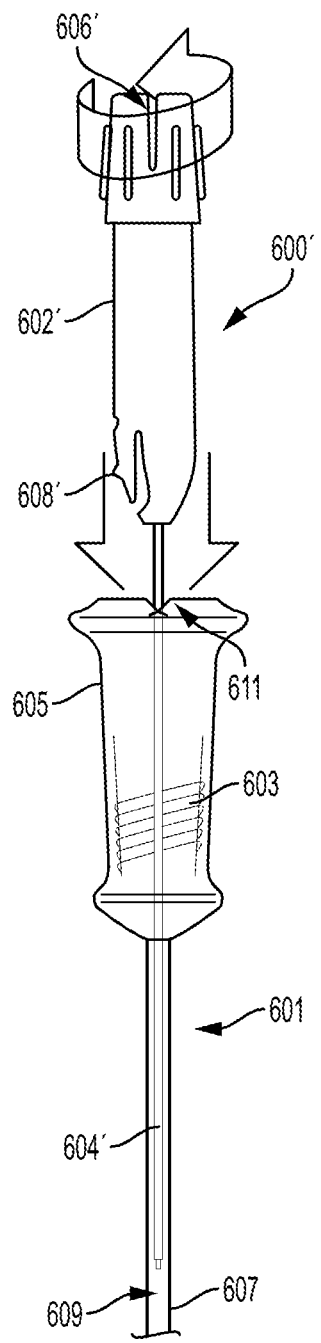
FIG. 33 is a side, partially transparent view of yet another embodiment of an inserter tool partially advanced into yet another embodiment of a guide device.
Figure 34:
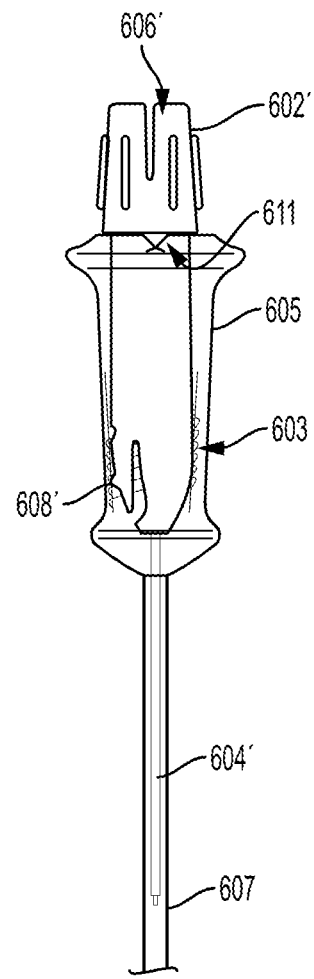
FIG. 34 is a side, partially transparent view of the inserter tool of FIG. 33 fully advanced into the guide device of FIG. 33.

FIGS. 33 and 34 illustrate another embodiment of an inserter tool 600', which has a second engagement feature 608' in the form of a ratchet or tooth in a distal portion thereof, configured to be inserted into a guide device 601, which has a first engagement feature 603 in the form of a thread in a distal portion thereof. The inserter tool 600' is generally configured and used similar to the inserter tool 32 of FIGS. 4-6, e.g., includes a handle 602', an elongate shaft 604' extending distally from the handle 602', a suture-engaging feature 606' in the form of a slit or cleat, and the second engagement feature 608'. The guide device 601 is generally configured and used similar to the guide device 10 of FIGS. 1-3, e.g., includes a handle 605, an elongate shaft 607 extending distally from the handle 605, an inner lumen 609 extending through the guide device 601, a suture-engaging feature 611 in the form of a slit or cleat, and the first engagement feature 603. The inserter tool 600' is configured to be advanced into the guide device's inner lumen 609 by being longitudinally translated therein in a distal direction, with the first and second engagement features 603, 608' becoming engaged with one another with the second engagement feature 608' ratcheting down the first engagement feature 603. The inserter tool 600' is configured to be removed from the guide device 601 by rotating the inserter tool 600' to advance the inserter tool 600' proximally out of the guide device 603.

Figure 35:
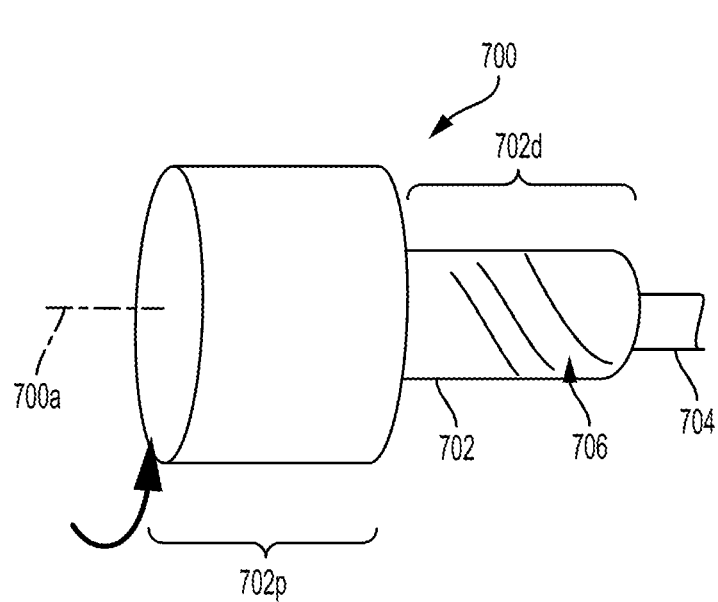
FIG. 35 is a side view of a proximal portion of still another embodiment of an inserter tool.

FIG. 35 illustrates another embodiment of an inserter tool 700 configured to be inserted into a guide device. The inserter tool 700 is generally configured and used similar to the inserter tool 32 of FIGS. 4-6, e.g., includes a handle 702, an elongate shaft 704 extending distally from the handle 702, and a second engagement feature 706, which is a thread. In this illustrated embodiment, the handle 702 includes a stationary proximal portion 702p and a movable distal portion 702d configured to move relative to the stationary proximal portion 702p. The movable distal portion 702d is configured to rotate about a longitudinal axis 700A of the inserter tool 700 relative to the stationary proximal portion 702p in response to engagement of the second engagement feature 706 with a first engagement feature in an inner lumen of a guide device in which the inserter tool 700 is being moved. When the second engagement feature 706 encounters the guide device's first engagement feature, e.g., a tooth or ratchet, the first engagement feature's engagement therewith can cause the handle's distal portion 702d to rotate as the first engagement feature threadably engages the thread 706. The inserter tool 700 can thus be advanced into the guide device with longitudinal or translational motion, e.g., pushing the inserter tool 700 downward or distally into the guide device's inner lumen, with the handle's distal portion 702d automatically rotating in response thereto when engaging the first engagement feature. The inserter tool 700 may thus be more quickly advanced distally in the guide device and/or may be easier to manipulate since for at least some users effecting translational motion may be easier and/or more intuitive than rotational motion.

Figure 37:
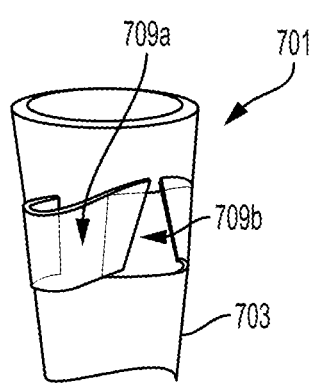
FIG. 37 is a perspective, partially transparent view of a portion of the guide device of FIG. 36.
Figure 36:
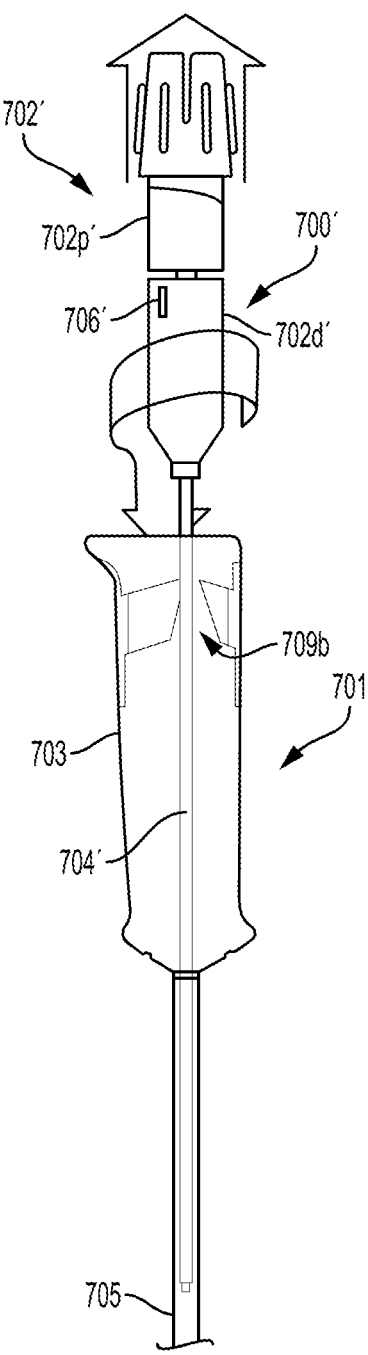
FIG. 36 is a side, partially transparent view of another embodiment of an inserter tool partially advanced into another embodiment of a guide device.

FIG. 36 illustrates another embodiment of an inserter tool 700' configured to be inserted into a guide device 701 and including a stationary proximal portion 702p' and a movable distal portion 702d' configured to move relative to the stationary proximal portion 702p'. The inserter tool 700' is generally configured and used similar to the inserter tool 32 of FIGS. 4-6, e.g., includes a handle 702', an elongate shaft 704' extending distally from the handle 702', and a second engagement feature 706', which is a protrusion or bump. The guide device 701, which is also shown in FIG. 37, is generally configured and used similar to the guide device 10 of FIGS. 1-3, e.g., includes a handle 703, an elongate shaft 705 extending distally from the handle 703, an inner lumen 705 extending through the guide device 701, a suture-engaging feature 707, and a first engagement feature 709a, 709b in the form of a pair of tapered grooves or channel that taper in opposite directions.

Referring again to FIGS. 4-6, the elongate shaft 36 of the guide device 32 can have a variety of sizes, shapes, and configurations. The elongate shaft 36 has a proximal end 36p that is mated to a distal end 34d of the handle 34 and has a distal end 36d (see FIG. 6) that is configured to releasably couple to an anchor, e.g., a knotless suture anchor. The shaft 36 has an anchor-engaging feature 52 at its distal end 36d that is configured to facilitate engagement of the shaft 36 with the anchor. The anchor-engaging feature 52 in this illustrated embodiment has a hexagonal cross-sectional shape for insertion into a hex-shaped proximal opening in the anchor. The anchor-engaging feature 52 can, in other embodiments, have a different shape, such as a cylindrical shape or fork-shaped (e.g., a pair of distally extending pins, etc.).

In an exemplary embodiment, a cross-sectional shape of the shaft 36 corresponds to a cross-sectional shape of the inner lumen 16 into which the shaft 36 is to be inserted. The shaft 36 in the illustrated embodiment has a circular cross-sectional shape that corresponds to the circular cross-sectional shape of the guide device's inner lumen 16. In other embodiments, the lumen 16 and the inserter tool's elongate shaft 36 can have another corresponding cross-sectional shape, e.g., rectangular, square, oval-shaped, triangular, etc. In at least some embodiments, the lumen 16 and the inserter tool's elongate shaft 36 can have different cross-sectional shapes, such as the lumen 16 having a triangular cross-sectional shape and the shaft 36 having a circular cross-sectional shape.

The inserter tool 32 can be made from any of a variety of materials. In an exemplary embodiment, the inserter tool 32 is made from plastic or polymer, such as acrylonitrile butadiene styrene (ABS), polycarbonate, polypropylene, etc. Additionally, in an exemplary embodiment, the inserter tool 32 is configured to be disposable, e.g., used with a single patient and then disposed per appropriate medical tool disposal procedures.

Figure 38:
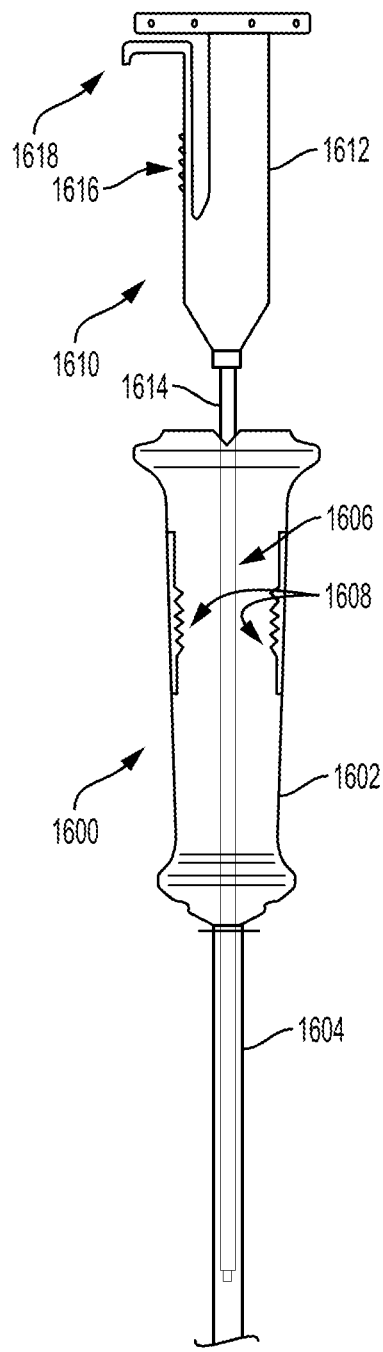
FIG. 38 is a side, partially transparent view of another embodiment of an inserter tool partially advanced into another embodiment of a guide device.
Figure 39:
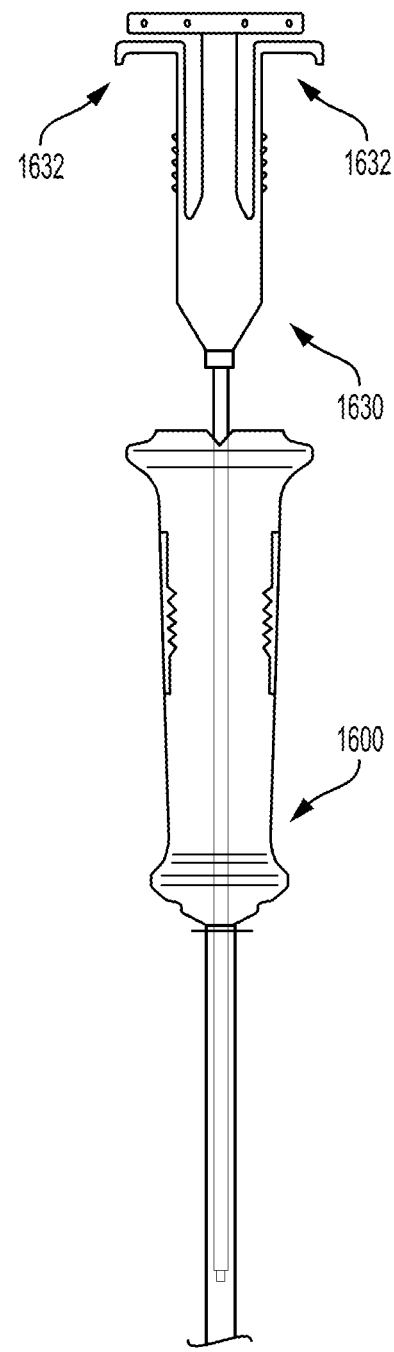
FIG. 39 is a side, partially transparent view of yet another embodiment of an inserter tool partially advanced into the guide device of FIG. 38.

FIG. 38 illustrates another embodiment of a guide device 1600 configured to receive therein an inserter tool 1610. The guide device 1600 is configured and used similar to the guide device 10 of FIGS. 1-3, e.g., includes a handle 1602, an elongate shaft 1604 extending distally from the handle 1602, an inner lumen 1606 extending through the guide device 1600, a suture-engaging feature (which is obscured), and a first engagement feature 1608 in the form of a ratchet or tooth on an inner wall that defines the guide device's inner lumen 1606. The inserter tool 1610 is generally configured and used similar to the inserter tool 32 of FIGS. 4-6, e.g., includes a handle 1612, an elongate shaft 1614 extending distally from the handle 1612, a second engagement feature 1616 in the form of a ratchet or tooth, and a quick release feature 1618 in the form of a single tab. The inserter tool 1610 is configured to be advanced into the guide device's inner lumen 1606 by being longitudinally translated therein in a distal direction, with the first and second engagement features 1608, 1616 becoming engaged with one another. The inserter tool 1610 is configured to be removed from the guide device 1600 by actuation of the quick release feature 1618, e.g., by the tab being pushed radially inward, which then allows the inserter tool 1610 to be pulled proximally out of the guide device 1600. FIG. 39 illustrates another embodiment of an inserter tool 1630 configured to be received by the guide device 1600 of FIG. 38. The inserter tool 1630 is similar to the inserter tool 1610 of FIG. 38 except that its quick release feature 1632 includes a pair of tabs instead of a single tab.

Figure 40:
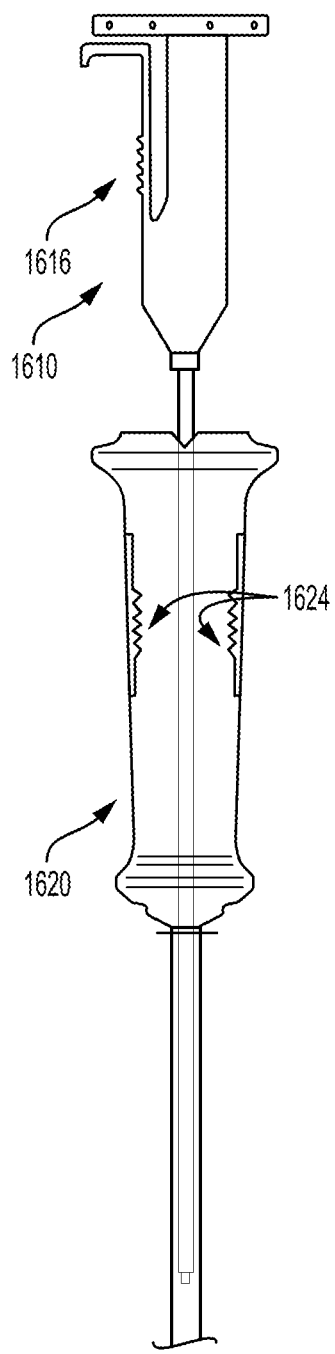
FIG. 40 is a side, partially transparent view of the inserter tool of FIG. 38 partially advanced into yet another embodiment of a guide device.
Figure 41:
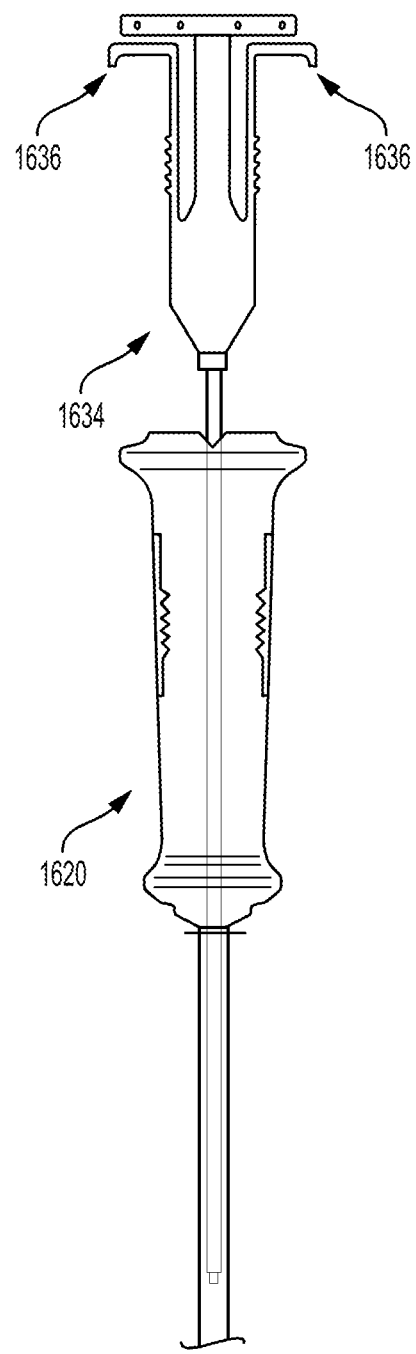
FIG. 41 is a side, partially transparent view of yet another embodiment of an inserter tool partially advanced into the guide device of FIG. 40.

FIG. 40 illustrates another embodiment of a guide device 1620 configured to receive therein the inserter tool 1610 of FIG. 38. The guide device 1620 is similar to the guide device 1600 of FIG. 38 except that its first engagement feature 1624 is a thread configured to engage the inserter tool's second engagement feature 1616. FIG. 41 illustrates another embodiment of an inserter tool 1634 configured to be received by the guide device 1620 of FIG. 40. The inserter tool 1634 is similar to the inserter tool 1610 of FIG. 38 except that its quick release feature 1636 includes a pair of tabs instead of a single tab.

Figure 42:
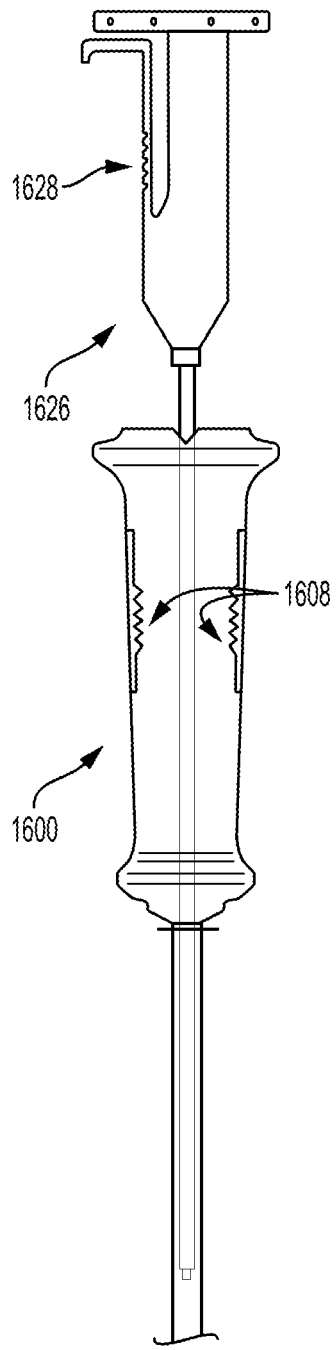
FIG. 42 is a side, partially transparent view of still another embodiment of an inserter tool partially advanced into the guide device of FIG. 39.
Figure 42A:
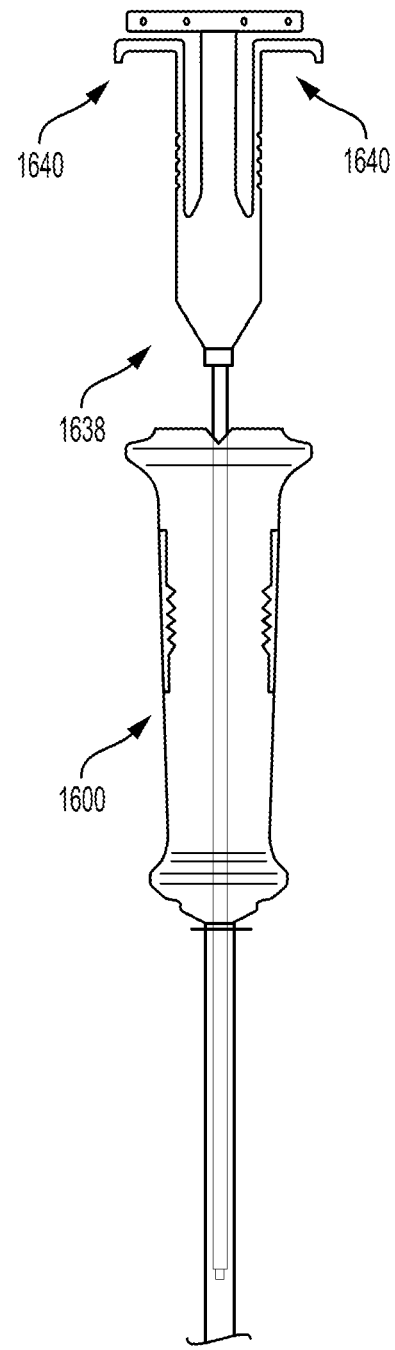
FIG. 42A is a side, partially transparent view of yet another embodiment of an inserter tool partially advanced into the guide device of FIG. 39.

FIG. 42 illustrates another embodiment of an inserter tool 1626 configured to be received by the guide device 1600 of FIG. 38. The inserter tool 1626 is similar to the inserter tool 1610 of FIG. 26 except that its second engagement feature 1628 is a thread configured to engage the guide device's first engagement feature 1608. FIG. 42A illustrates another embodiment of an inserter tool 1638 configured to be received by the guide device 1600 of FIG. 38. The inserter tool 1638 is similar to the inserter tool 1626 of FIG. 42 except that its quick release feature 1640 includes a pair of tabs instead of a single tab.

Figure 43:
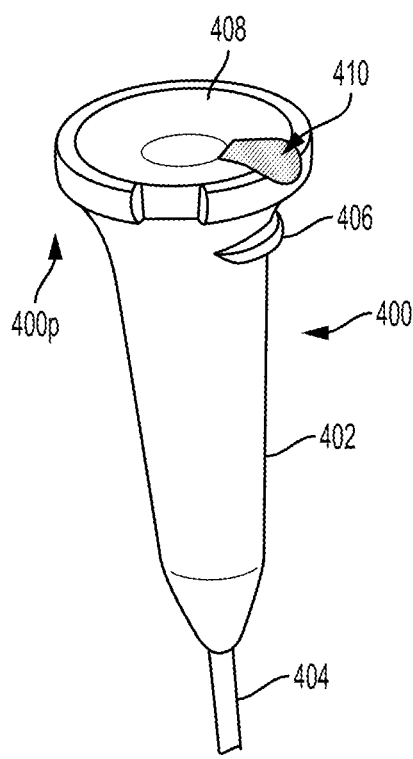
FIG. 43 is a perspective view of a proximal portion of yet another embodiment of an obturator.
Figure 44:
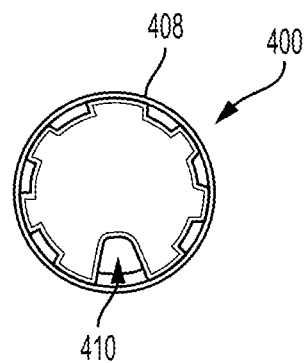
FIG. 44 is a top view of the obturator of FIG. 43.

FIGS. 43-44 illustrate another embodiment of an obturator 400 configured to receive therein an inserter tool and a guide device. The obturator 400 is configured and used similar to the obturator 202' of FIG. 26, e.g., includes a handle 402, an elongate shaft 404 extending distally from the handle 402, and an inner lumen extending through the obturator 400. The obturator 400 also includes a suture-engaging feature 406 that in this illustrated embodiment is a protrusion on an outer surface of the obturator 400 around which a suture extending through the obturator's inner lumen can be wrapped or tied to releasably engage the suture to the obturator 400. However, the suture-engaging feature 406 can have other configurations, such as a partial thread.

The obturator 400 has a proximal cover 408 at its proximal end 400*p*. The proximal cover 408 may help prevent fluid and/or other matter from exiting the inner lumen through the obturator's proximal end 400*p*, where it may interfere with handling of the obturator 400, guide device, and/or the inserter tool inserted therein. The cover 408 includes a plurality of flaps that allows a tool, such as a drill, guide device, or an inserter tool, to be advanced through the cover 408 to enter the obturator's inner lumen. The cover 408 has a cut-out 410 therein that is in communication with the obturator's inner lumen. The cut-out 410 is configured to allow passage of a suture therethrough. In this way, a suture extending through the obturator's inner lumen can exit the inner lumen through the cut-out 410 and be selectively secured as desired to the suture-engaging feature 406 of the obturator 400, a suture-engaging feature of the inserter tool, a suture-engaging feature of the guide device, and an anchor to be inserted into a patient using the inserter tool. As shown in FIG. 43, the cut-out 410 is aligned radially with the suture-engaging feature 406, which may help a suture extending through the obturator's inner lumen engage the suture-engaging feature 406 at a convenient approach angle that helps prevent the suture from tangling or being obstructive of holding the obturator 400 and/or any tools inserted therein.

In at least some embodiments, an inserter tool can include one or more suture-seating grooves formed on an outer surface thereof. The one or more suture-seating grooves can allow a suture extending through an inner lumen of a guide device into which the inserter tool is advanced to be seated therein, which may help protect the suture from damage from the inserter tool, e.g., from the second engagement feature thereof.

Figure 45:
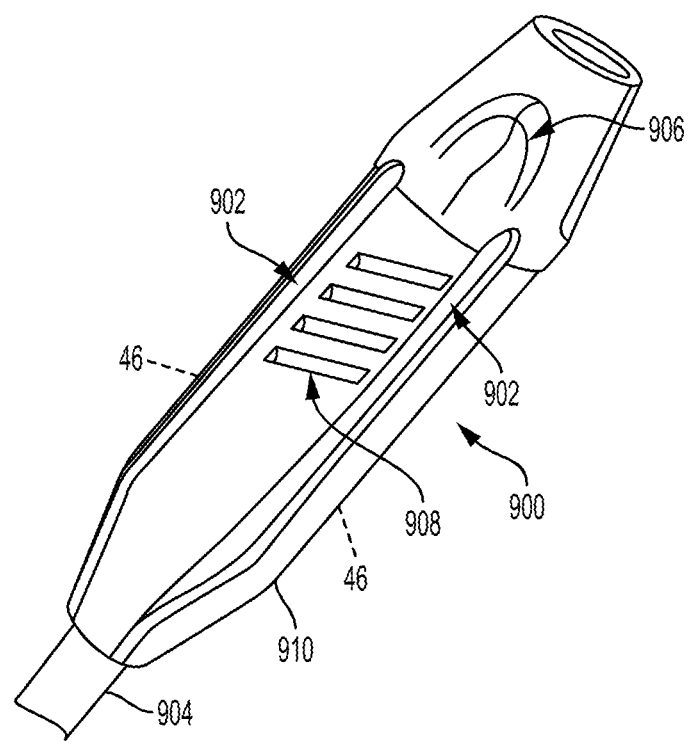
FIG. 45 is a perspective view of a proximal portion of another embodiment of an inserter tool.

FIG. 45 illustrates one embodiment of an inserter tool 900 including one or more suture-seating grooves 902 formed in an outer surface thereof and extending longitudinally therealong. The inserter tool 900 has three suture-seating grooves 902 in the illustrated embodiment but can have another number of suture-seating grooves. The inserter tool 900 is generally configured and used similar to the inserter tool 32 of FIGS. 4-6, e.g., includes a handle 910, an elongate shaft 904 extending distally from the handle 902, a suture-engaging feature 906 in the form of a slot or cut-out, and a second engagement feature 908, which is a thread. As shown in FIG. 46, each of the suture-seating grooves 902 has a same depth 902*d*, which is generally deep enough to allow a full diameter of a suture to be seated in the suture-seating groove 902. For example, the depth 902*d* can be about 5 mm. A person skilled in the art will appreciate that the depth may not be precisely at a value (e.g., 5 mm) but nevertheless be considered to be about that value due to any number of factors, such as manufacturing tolerances and sensitivity of measurement equipment. As shown in FIG. 47, the inserter tool 900 has two suture-engaging features 906 on opposed sides of the handle 910. Having more than one suture-engaging feature 906 may provide more options to medical personnel for temporary securing of suture.

As mentioned above, suture-engaging features can have a variety of configurations. FIG. 48 illustrates an embodiment of an inserter tool with a plurality of suture-engaging features 1000 in the form of notches arranged radially around the inserter tool's proximal end. One of the notches 1000 is shown having a suture 1002 seated therein. The inserter tool has five suture-engaging features 1000 in this illustrated embodiment but can have another number.

FIG. 49 illustrates another embodiment of an inserter tool with a plurality of suture-engaging features 1100 in the form of slits or cleats formed in the inserter's tools proximal end. The suture-engaging features 1100 are similar to the suture-engaging feature 38 of the inserter tool of FIGS. 4-6 except that the inserter tool of FIG. 49 has two slits or cleats that are offset from one another to form an "X" shape on the inserter tool's proximal surface.

FIG. 50 illustrates another embodiment of an inserter tool with a suture-engaging feature 1200 in the form of a T-bar configured to receive a suture wrapped or tied therearound. The T-bar extends proximally from a proximal surface of the inserter tool.

FIG. 51 illustrates another embodiment of an inserter tool with a plurality of suture-engaging features 1300 in the form of a pegs that extend radially outward from a proximal end of the inserter tool. The inserter tool has two pegs 1300 in this illustrated embodiment but can have another number, e.g., one or more.

Figure 52:
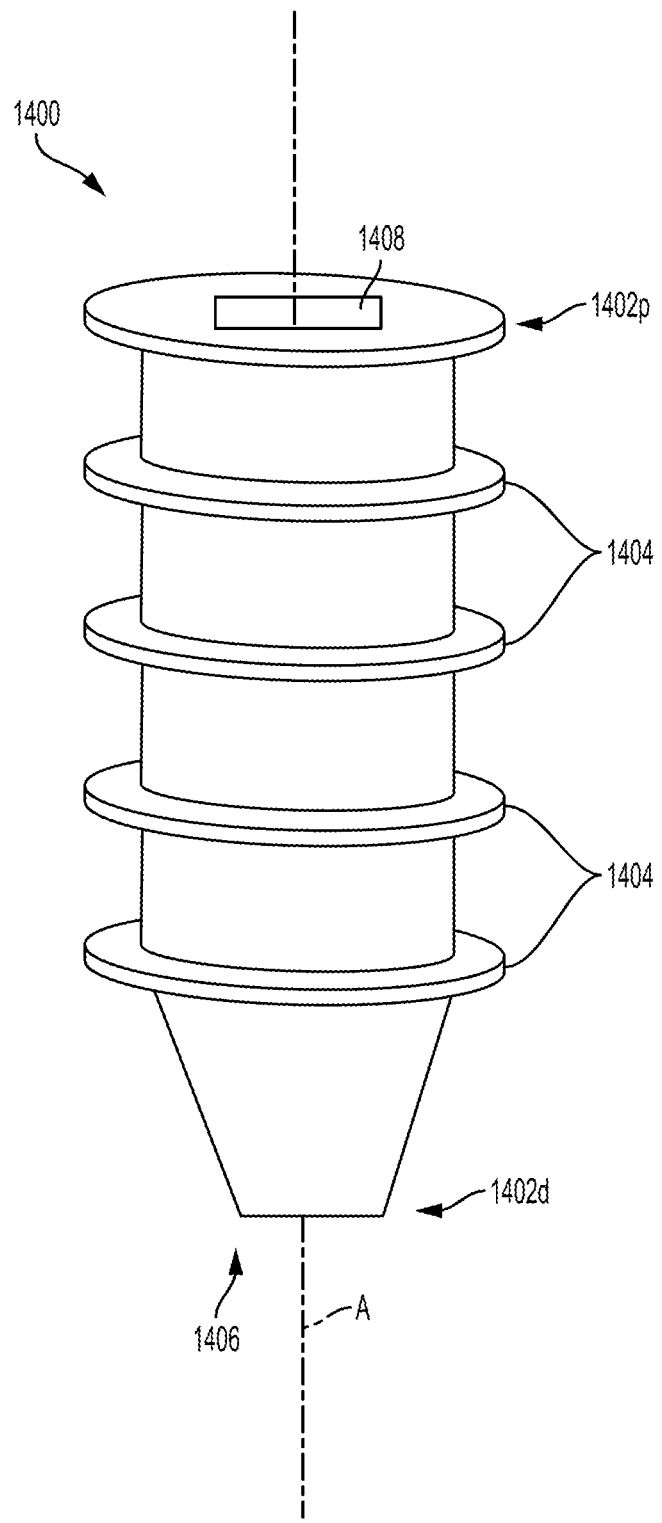
FIG. 52 is a perspective view of one embodiment of a suture anchor.

Suture anchors having a variety of different constructions can be used with the inserter tools and guide devices disclosed herein. A person skilled in the art will appreciate that various suture anchors known in the art can be used in connection with the systems, devices, and methods disclosed herein. By way of example, FIG. 52 illustrates one embodiment of a suture anchor 1400. As shown, the suture anchor 1400 is generally elongate with a longitudinal axis A extending between a proximal end 1402p and a distal end 1402d of the anchor 1400. The suture anchor 1400 can have at least one bone-engaging surface feature configured to engage bone, such as a plurality of ribs 1404 arranged axially along the anchor 1400.

The suture anchor 1400 can have features for receiving a suture therein. The suture anchor 1400 in this illustrated embodiment has an inner lumen 1406, that extends between the proximal and distal ends 1402p, 1402d along the longitudinal axis A of the suture anchor 1400, for receiving a suture. In another embodiment, an aperture (not shown) can extend at least partially through the suture anchor 1400 along an axis transverse to the longitudinal axis A. As will also be appreciated by a person skilled in the art, the suture anchor 1400 can alternatively have one or more apertures or openings disposed at any location on the anchor 1400, such as on a sidewall of the anchor 1400. Such apertures can form a pathway for receiving a suture that can be curved, or of any other shape.

The suture anchor 1400 can have a mating feature 1408 positioned on the proximal end 1402p of the anchor 1400 and configured to mate with a distal end of an inserter tool, e.g., by having a distal tip thereof inserted into the mating feature 1408.

The suture anchor 1400 is configured as a knotless suture anchor that allows a user to thread the anchor 1400 with suture and form a loop without tying a knot. By way of non-limiting example, a suture (not shown) can be threaded through the anchor 1400 by inserting one terminal end of the suture through the proximal end 1402p of the anchor, passing it distally, moving around the distal end 1402d of the anchor 1400, and out through a sidewall of the anchor 1400. A suture threader (not shown) can also be used to thread the suture through suture anchor 1400.

A kit can be provided that includes at least one guide device and a plurality of inserter tools each configured to be advanced through the guide device to deliver a suture anchor to a surgical site. Each of the inserter tools can be configured to be used with a differently sized anchor, e.g., each have a distal end configured to be releasably coupled to a particular size of anchor. A surgeon (or other medical personnel) can thus select from the kit which of the inserter tools to use with the guide device based on the anchor to be deployed in a particular patient In an exemplary embodiment, the kit includes a single guide device, with a surgeon (or other medical personnel) merely selecting a preferred one of the inserter tools to use with the one guide device. In at least some embodiments, the kit can include at least one anchor configured to be deployed using one or more of the plurality of tools inserter tools, and/or the kit can include at least one suture configured to be coupled to the anchor deployed using the guide device and a selected one of the plurality of inserter tools. In at least some embodiments, the kit can also include at least one obturator.

Various methods for reattaching soft tissue to bone are also provided herein. In general, in a surgical procedure a suture is coupled to tissue to be reattached, and an anchor having the suture coupled thereto is implanted in a bone hole at an attachment location. The suture is tensioned to pull the tissue toward the bone. The anchor can be configured to lock and prevent sliding of the suture, thereby reattaching the tissue to the bone.

In use, the procedure usually begins by preparing a patient for surgery and making one or more appropriately sized incisions at a desired location. In a minimally invasive procedure, one or more obturators or cannulas (not shown) can be positioned in the incisions to provide access to the surgical site. A person skilled in the art will also appreciate that one or more viewing devices, e.g., scopes, can be placed in one or more of the incisions to allow medical personnel to view the surgical site from outside the patient's body.

Figure 53:
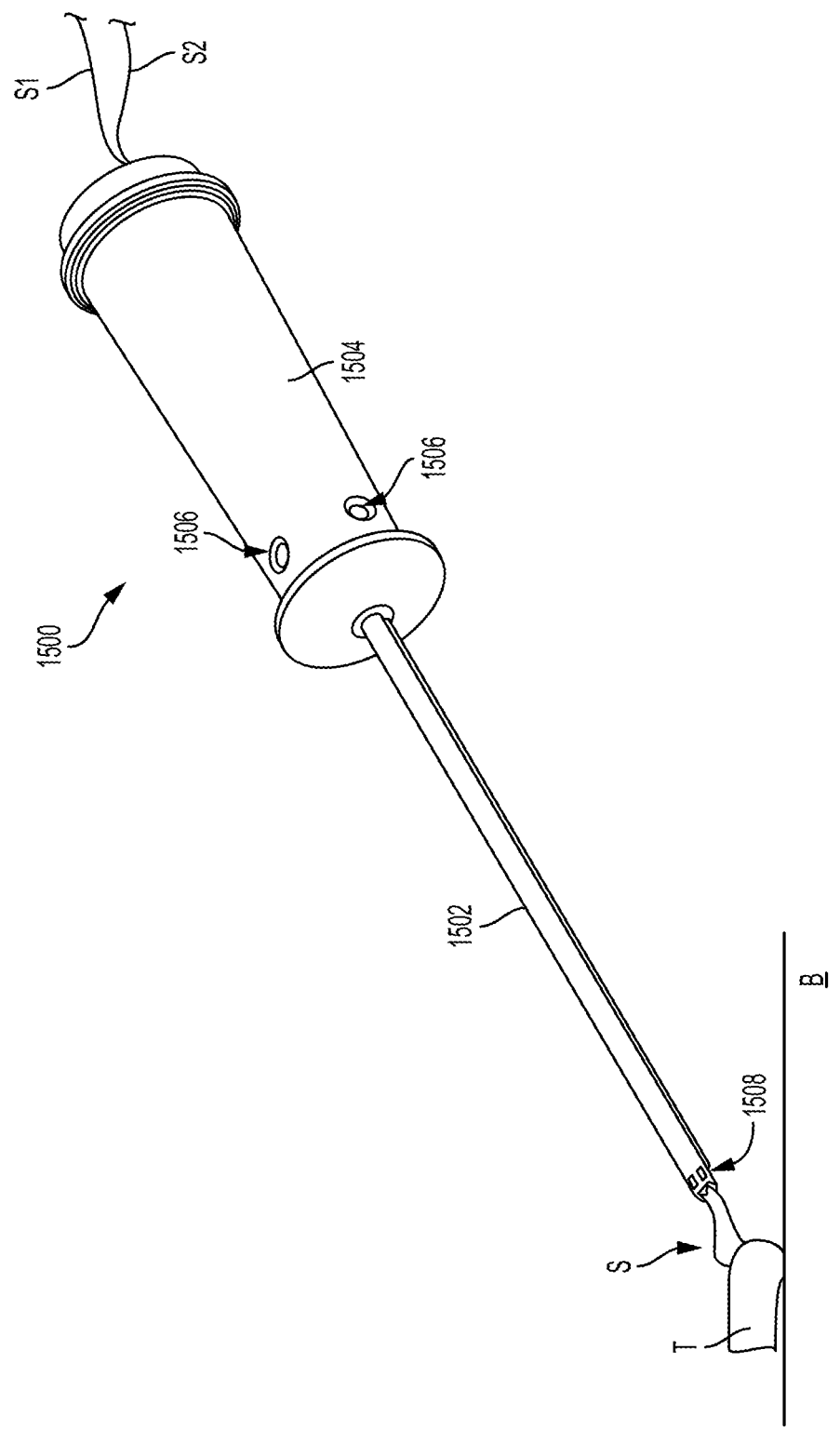
FIG. 53 is a perspective view of another embodiment of a guide device with a suture extending therethrough and coupled to tissue.

Once the patient is prepared for surgery, with reference to FIG. 53, a length of suture S is passed into the patient's body and passed through soft tissue T that is to be surgically reattached to bone B. As shown in FIG. 53, the suture S can be passed through tissue T such that limbs or free ends S1, S2 of the suture S are positioned outside of the patient's body. A person skilled in the art will appreciate that the suture S can be passed through the tissue T using any known surgical technique, such as by mattress and cinch loop methods. With the suture S so positioned, a guide device (e.g., guide device 1500 is shown by way of example) is positioned within the surgical site with the suture S being positioned within an inner lumen extending through the guide device 1500. This can be accomplished by a variety of known techniques, including by passing a suture passer (not shown) into the lumen at a distal end of the guide device's elongate shaft 1502 and out of the inner lumen at a proximal end of the guide device's handle 1504 such that the two limbs S1, S2 of the suture S extend out of the handle 1504. The guide device 1500 is generally configured and used similar to the guide device 10 of FIGS. 1-3, e.g., includes a handle 1504, an elongate shaft 1502 extending distally from the handle 1504, an inner lumen extending through the guide device 1500, one or more irrigation holes 1506, and a first engagement feature (obscured in FIG. 53) extending radially inward from an inner wall that defines the guide device's inner lumen.

Once the suture S is positioned through the guide device 1500, the suture limbs S1, S2 extending from the handle 1504 can be tensioned. The guide device 1500 in this illustrated embodiment includes a relief cut-out 1508 in a distal end of the shaft 1502, and the suture S can be tensioned so as to cause the suture S to sit within the relief cut-out 1508. Exemplary embodiments of relief cut-outs are further described in previously mentioned U.S. Pat. Pub. No. 2016/0310125 entitled "Knotless Suture Anchor Guide" filed Apr. 23, 2015. The guide device 1500 in this illustrated embodiment includes a secondary offset region, and the suture S can be tensioned to be seated in the secondary offset region along the entire length of the shaft 1502. The limbs S1, S2 extending out of the handle 1504 can be engaged with a suture-engaging feature (not shown) of the guide device 1500 to maintain and prevent sliding of the suture S. In an exemplary embodiment, the relief cut-out 1508, the secondary region, and the suture-engaging feature are all longitudinally aligned and are all positioned at the same radial location around a perimeter of the shaft 1502 so as to maintain the suture S off to one side of the shaft 1502.

Figure 54:
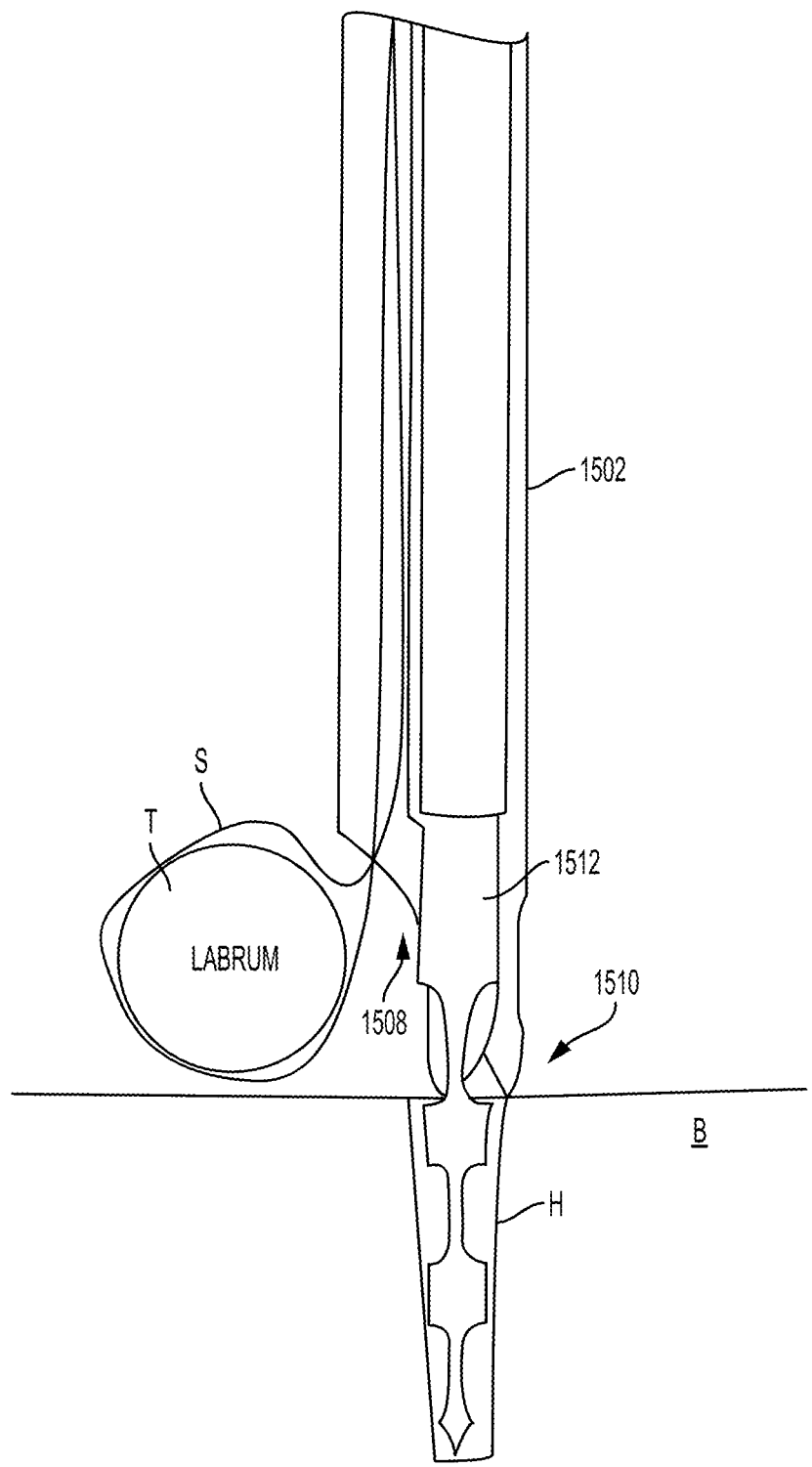
FIG. 54 is a side view of a distal portion of the guide device, suture, and tissue of FIG. 53.

With the suture S tensioned and positioned as desired relative to the secondary offset region (if present) and suture-engaging feature (if present) of the guide device 1500, a bone engaging surface feature 1510, which is this illustrated embodiment are bone engaging teeth, on the distal end of the guide device's shaft 1502 can be positioned to abut bone B, as shown in FIG. 54. The shaft 1502 should be oriented such that the relief cut-out 1508 (if present) faces the tissue T being reattached, as shown in FIG. 54. As so positioned, the suture S adjacent to the distal end of the shaft 1502 will extend across the relief cut-out 1508 toward the tissue T. The suture S will thus be pulled up and out of the way of the bone surface. If the relief cut-out 1508 includes two notches formed therein, each limb of the suture S can be seated in a notch so as to prevent twisting of stacking of the suture S as it extends through the inner lumen of the guide device 1500. A drill 1512 can then be passed through the shaft 1502 to form a hole H in the bone B. A cutting tip on the drill can be rotated, manually or by a motor, to advance the cutting tip through the bone B to form the hole H. During drilling, a user (or surgical robot) can grasp the handle 1504 of the guide device 1500 to maintain the position of the guide device 1500 relative to the bone B. Grasping of the suture S is unnecessary since it is held by the suture-engaging feature. Since the drill bit only occupies the primary region of the shaft 1502 and the suture S is maintained in the secondary offset region, in this illustrated embodiment with primary and secondary shaft regions, as shown in FIG. 54, the drill bit flutes will not contact or cause damage to the suture S.

Figure 55:
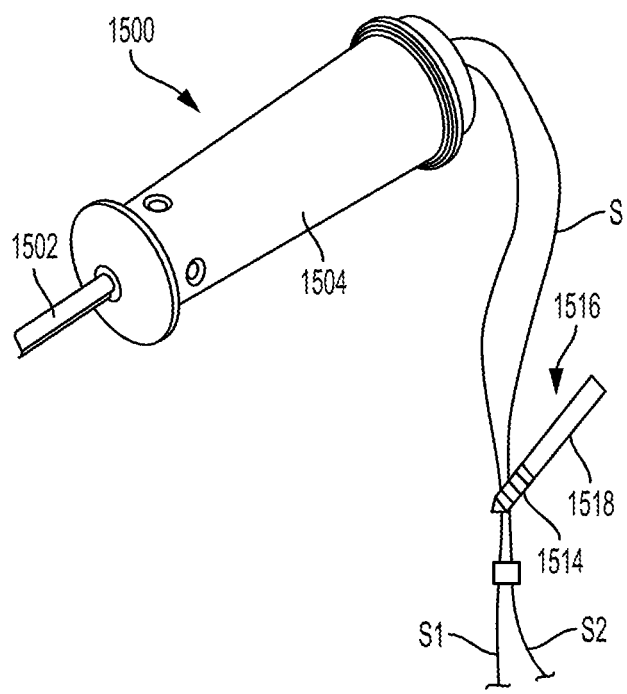
FIG. 55 is a perspective view of the guide device, suture, and tissue of FIG. 53 with an anchor coupled to trailing ends of the suture and the anchor coupled to another embodiment of an inserter tool.

Once the bone hole H is formed, the drill 1512 can be removed, leaving the guide device 1500 in contact with the bone surface. A downward force can be applied to the guide device 1500 to cause the bone engaging teeth 1508 to dig into the bone surface to hold the guide device 1500 in position against the bone B while the drill 1512 is removed. After the suture S is passed through the guide device 1500, and either before or after the bone hole H is formed, an anchor, e.g., anchor 1514 is shown, can be mated to the trailing limbs S1, S2 of the suture S. This can be achieved by threading the suture S onto the anchor 1514 as known based on the configuration of the anchor 1514. With the anchor 1514 mated to the suture S, as shown in FIG. 55, the anchor 1514 can be mounted onto an inserter tool, e.g., inserter tool 1516 (only a distal portion of which is shown for clarity of illustration), such as by inserting a distal tip of the inserter tool 1516 into a mating feature of the anchor 1514. The inserter tool 1516 is generally configured and used similar to the inserter tool 32 of FIGS. 4-6, e.g., includes a handle (not shown), an elongate shaft 1518 extending distally from the handle, and a second engagement feature (not shown) configured to engage the guide device's first engagement feature.

Figure 56:
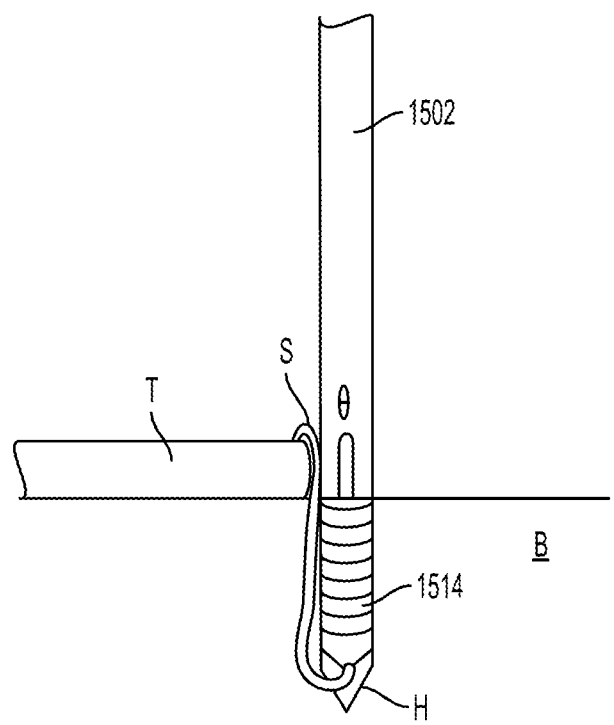
FIG. 56 is a side view of a distal portion of the guide device of FIG. 55 with the anchor implanted in a bone hole and the suture tensioned to reattach the tissue to bone.

In order to implant the anchor 1514, the suture S can be tensioned to position the tissue T at a desired location relative to the bone B, and while maintaining tension of the suture S, the inserter tool 1516 can be manipulated to slide the anchor 1514 along the suture S through the guide device 1500 and into the bone hole H, as shown in FIG. 56. As the inserter tool 1516 is passed through the guide device 1500, the anchor 1514 can slide along the suture S so that the terminal ends S1, S2 remain outside of the patient's body. Continued alignment between the shaft 1502 of the guide device 1500 and the bone hole H as the anchor 1514 is inserted therein ensures that a longitudinal axis of the anchor 1514 is aligned with a longitudinal axis of the bone hole H. Such alignment minimizes the risk of inserting the anchor 1514 at an improper angle, which may damage the bone B and/or anchor 1514 and/or may cause the anchor 1514 to fail. As discussed above, the distal advancement of the inserter tool 1516 through the guide device 1500 will automatically cause engagement of the respective engagement features of the guide device 1500 and inserter tool 1516.

A user can monitor the position of the anchor 1514 within the guide device 1500 using a scoping device or other visualization instrument that is focused on one or more viewing windows in the shaft 1502. Once the anchor 1514 is partially seated within the hole H, the terminal limbs S1, S2 of the suture S can be further pulled to tension the suture S and thereby pull the attached tissue T closer to the anchor 1514, and thus, to the position of bone B to which it is to be secured. The anchor 1514 can be driven into the hole H, such as by tapping the proximal end of the inserter tool 1516 with a mallet or other tool. This action serves to lock the suture S between an outer surface of the anchor 1514 and an inner surface of the hole H. As will be appreciated by a person skilled in the art, the anchor 1514 can lock the suture S in other ways, such as using a set screw or internal interference feature.

After the anchor 1514 is fully seated in the hole H, as shown in FIG. 56, the inserter tool 1516 can be removed from the guide device 1500 as discussed above, such as by being rotated relative thereto. The removal of the inserter tool 1516 from the guide device 1500 will automatically release the anchor 1514 from the inserter tool 1516, as discussed above, with the anchor 1514 remaining in the bone B. The guide device 1500 and inserter tool 1516 can be removed from the surgical site, and the ends of the suture S can be trimmed if desired. The inserter tool 1516 can be fully removed from the guide device 1500 before the guide device 1500 is removed from the surgical site. Alternatively, the inserter tool 1516 can be partially removed from the guide device 1500 before the guide device 1500 is removed from the surgical site, such as by the inserter tool 1516 being moved enough proximally in the guide device 1500 to disengage the first and second engagement features of the guide device 1500 and inserter tool 1516, thereby indicating that the anchor 1514 has been released from the inserter tool 1516. The disengagement of the first and second engagement features can be tactilely and/or audibly detected by a user, as discussed above.

The devices, systems, and methods described above can be used for a variety of tissue attachment procedures including, by way of non-limiting example, arthroscopic shoulder surgery. For example, the suture can be passed through the labrum and the drill guide can also be used to lever the humeral head away from the glenoid cavity to gain access to the glenoid rim prior to drilling the bone. A person skilled in the art will appreciate that the guide device can be used in connection with a guide wire instead of or in addition to a suture. The guide wire can be extend through a guide device's shaft during drilling, and a suture anchor can subsequently be advanced along the guide wire during insertion thereof through the guide device.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

The invention described herein can be processed before use. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that devices disclosed herein are sterilized. This can be done by any number of ways known to those skilled in the art including beta or gamma radiation, ethylene oxide, steam, and a liquid bath (e.g., cold soak).

A person skilled in the art will appreciate that the implementations described herein have application in conventional minimally-invasive and open surgical instrumentation as well application in robotic-assisted surgery.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical system, comprising:
   a guide device having a handle and a first elongate shaft extending distally from the handle, the guide device having an inner lumen extending therethrough, the guide device having a first engagement feature on an inner wall of the guide device that defines the inner lumen, and the guide device being configured to guide a drill to a surgical site through the inner lumen thereof; and
   an inserter tool having a second elongate shaft configured to be advanced distally through the inner lumen of the guide device with an anchor releasably coupled to a distal end of the second elongate shaft, the second elongate shaft having a second engagement feature on an outer surface thereof that is configured to engage the first engagement feature during the distal advancement of the second elongate shaft through the inner lumen of the guide device, and disengagement of the first and second engagement features is configured to automatically cause the anchor to be released from the distal end of the second elongate shaft.

2. The system of claim 1, wherein the second elongate shaft is configured to be advanced distally into the inner lumen of the guide device in a first type of motion relative to the guide device, and the second elongate shaft is configured to be removed from the inner lumen of the guide device in a second, different type of motion relative to the guide device.

3. The system of claim 2, wherein the first and second engagement features are configured to cooperate when engaged with one another to prevent the second elongate shaft from being removed from the inner lumen of the guide device using the first type of motion.

4. The system of claim 2, wherein the first type of motion is longitudinal translation of the second elongate shaft through the inner lumen, and the second type of motion is rotation of the second elongate about a longitudinal axis of the second elongate shaft.

5. The system of claim 4, wherein the first and second engagement features are configured to cooperate when engaged with one another to prevent the second elongate shaft from being removed from the inner lumen of the guide device by longitudinally translating through the inner lumen in a proximal direction.

6. The system of claim 1, wherein one of the first and second engagement features is a thread, and the other of the first and second engagement features is a tooth configured to threadably engage the thread.

7. The system of claim 1, wherein the inserter tool has a handle with the second elongate shaft extending distally therefrom, the handle of the inserter tool being configured to abut the handle of the guide device when inserted therein to thereby prevent further distal advancement of the second elongate shaft through the inner lumen of the guide device.

8. The system of claim 7, wherein the first and second engagement features are configured to be engaged when the handle of the inserter tool is abutting the handle of the guide device.

9. The system of claim 1, further comprising a suture configured to extend through the inner lumen of the guide device, the inserter tool being configured to be advanced distally through the inner lumen of the guide device over the suture with the suture coupled to the anchor.

10. The system of claim 1, further comprising at least one additional inserter tool having an elongate shaft and being configured to be advanced distally through the inner lumen of the guide device with an anchor releasably coupled to a distal end of the elongate shaft, each of the inserter tools being configured to releasably couple to a differently sized anchor.

11. The system of claim 1, further comprising the anchor releasably coupled to the distal end of the second elongate shaft.

12. A surgical system, comprising:
   a guide device having a first handle and a first elongate shaft extending distally from the first handle, the guide device having an inner lumen extending therethrough, and the guide device being configured to guide a drill through the inner lumen to allow the drill to drill a hole in bone; and
   an inserter tool having a second handle and a second elongate shaft extending distally from the second handle,
   wherein the second elongate shaft is configured to be advanced distally through the inner lumen of the guide device, with an anchor releasably coupled to a distal end of the second elongate shaft, by being one of (1) longitudinally translated through the inner lumen and (2) rotated about a longitudinal axis of the second elongate shaft relative to the guide device, and
   wherein the second elongate shaft is configured to be removed from the inner lumen of the guide device when the first and second handles are abutting one another only by being the other of (1) longitudinally translated through the inner lumen and (2) rotated about the longitudinal axis of the second elongate shaft relative to the guide device.

13. The system of claim 12, wherein the guide device is configured such that removal of the second elongate shaft of the inserter tool from the inner lumen of the guide device automatically releases the anchor from the distal end of the second elongate shaft.

14. The system of claim 12, wherein the first elongate shaft has a first engagement feature on an inner surface thereof, and
the inserter tool has a second engagement feature on an outer surface thereof that is configured to
automatically engage the first engagement feature during the distal advancement of the of the second elongate shaft through the inner lumen of the guide device in the one of (1) being longitudinally translated through the inner lumen and (2) being rotated about the longitudinal axis of the second elongate shaft relative to the guide device, and
automatically disengage from the first engagement feature in response to the other of (1) the second elongate shaft longitudinally translating through the inner lumen and (2) rotating about the longitudinal axis of the second elongate shaft relative to the guide device to remove the second elongate shaft from the inner lumen of the guide device.

15. The system of claim 14, wherein one of the first and second engagement features is a thread, and the other of the first and second engagement features is a tooth configured to threadably engage the thread.

16. The system of claim 15, wherein the first engagement feature is a thread and the second engagement feature is a tooth such that the second elongate shaft is configured to be advanced distally through the inner lumen of the guide device by being longitudinally translated therethrough, and the second elongate shaft is configured to be removed from the inner lumen of the guide device when the first and second handle are abutting one another only by being rotated about the longitudinal axis of the second elongate shaft relative to the guide device.

17. The system of claim 12, wherein the first and second handles are configured to abut one another and thereby prevent further distal advancement of the second elongate shaft through the inner lumen of the guide device and position the anchor at a predetermined position relative to the guide device.

18. The system of claim 12, further comprising the anchor releasably coupled to the distal end of the second elongate shaft.

19. A surgical method, comprising:
passing a suture through tissue to be anchored to bone;
passing a trailing end of the suture extending from the tissue through an inner lumen in a first elongate shaft of a guide device;
advancing a drill through the inner lumen of the guide device to form a hole in the bone;
advancing a second elongate shaft of an inserter tool over the suture in the inner lumen and through the inner lumen of the guide device in a distal direction to position an anchor, which is coupled to the suture and is releasably coupled to a distal end of the second elongate shaft, in the hole,
wherein the first elongate shaft has a first engagement feature on an inner surface thereof, and the second elongate shaft has a second engagement feature on an outer surface thereof that automatically engages the first engagement feature during the advancement of the second elongate shaft through the inner lumen of the guide device, and
wherein the engagement of the first and second engagement features limits the advancement of the second elongate shaft to being only one of (1) longitudinal translation through the inner lumen of the guide device and (2) rotation about a longitudinal axis of the second elongate shaft relative to the guide device; and
removing the second elongate shaft from the inner lumen of the guide device by moving the second elongate shaft in a proximal direction, thereby automatically releasing the anchor from the distal end of the second elongate shaft such that the anchor remains in the hole with the suture coupled to and extending from the anchor,
wherein the engagement of the first and second engagement features limits the movement of the second elongate shaft in the proximal direction to being the other one of (1) longitudinal translation through the inner lumen of the guide device and (2) rotation about the longitudinal axis of the second elongate shaft relative to the guide device.

20. The method of claim 19, wherein the first engagement feature automatically disengages from the second engagement feature in response to the removal of the second elongate shaft from the inner lumen of the guide device.

21. The method of claim 19, wherein the second elongate shaft is advanced through the inner lumen of the guide device by being longitudinally translated therethrough in the distal direction, the second elongate shaft is removed from the inner lumen of the guide device by being rotated about the longitudinal axis of the second elongate shaft relative to the guide device, and the engagement of the first and second engagement features prevents the second elongate shaft from being removed from the inner lumen of the guide device by being longitudinally translated therethrough in the proximal direction.

22. The method of claim 19, wherein the second elongate shaft is advanced through the inner lumen of the guide device until a handle of the guide device abuts a handle of the inserter tool, the abutment of the handles indicating that the anchor is positioned within the hole, and the first and second engagement features being engaged when the handle of the guide device abuts the handle of the inserter tool.

23. The method of claim 19, wherein the second elongate shaft is advanced through the inner lumen of the guide device by being rotated about the longitudinal axis of the second elongate shaft relative to the guide device, the second elongate shaft is removed from the inner lumen of the guide device by being longitudinally translated therethrough in the distal direction, and the engagement of the first and second engagement features prevents the second elongate shaft from being removed from the inner lumen of the guide device by being rotated about the longitudinal axis of the second elongate shaft relative to the guide device.

* * * * *